US011866424B2

(12) United States Patent
Tang et al.

(10) Patent No.: US 11,866,424 B2
(45) Date of Patent: Jan. 9, 2024

(54) AGGREGATION-INDUCED EMISSION LUMINOGENS FOR PHOTODYNAMIC THERAPY

(71) Applicant: The Hong Kong University of Science and Technology, Hong Kong (CN)

(72) Inventors: Benzhong Tang, Hong Kong (CN); Wenhan Xu, Hong Kong (CN); Dong Wang, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 52 days.

(21) Appl. No.: 17/248,340

(22) Filed: Jan. 21, 2021

(65) Prior Publication Data

US 2021/0221799 A1 Jul. 22, 2021

Related U.S. Application Data

(60) Provisional application No. 62/995,270, filed on Jan. 22, 2020.

(51) Int. Cl.
*C07D 405/06* (2006.01)
*A61K 49/00* (2006.01)
*A61K 41/00* (2020.01)

(52) U.S. Cl.
CPC ........ *C07D 405/06* (2013.01); *A61K 41/0057* (2013.01); *A61K 49/0021* (2013.01)

(58) Field of Classification Search
CPC .............. C07D 405/06; A61K 41/0057; A61K 49/0021
See application file for complete search history.

(56) References Cited

U.S. PATENT DOCUMENTS 11,253,592 B2 * 2/2022 Tang .................... C07D 213/38
2018/0156811 A1 6/2018 Tang et al.

FOREIGN PATENT DOCUMENTS

| CN | 108055852 A | 5/2018 |
| CN | 110201165 A | 9/2019 |
| CN | 110790698 A | 2/2020 |
| WO | 2019080868 A1 | 5/2019 |

OTHER PUBLICATIONS

Marri et al., Dyes and Pigments, 2019, 165, p. 508-517. (Year: 2019).*
Ji et al., J. Mater. Chem., 2012, 22, p. 12375-12380. (Year: 2012).*
Wang et al. (Adv. Mater., 2018, 1802105). (Year: 2018).*
Guo, M.; Mao, H.; Li, Y.; Zhu, A.; He, H.; Yang, H.; Wang, Y.; Tian, X.; Ge, C.; Peng, Q.; Wang, X.; Yang, X.; Chen, X.; Liu, G.; Chen, H., Dual imaging-guided photothermal/photodynamic therapy using micelles. Biomaterials 2014, 35 (16), 4656-4666.
Hu, Q.; Gao, M.; Feng, G.; Liu, B., Mitochondria-Targeted Cancer Therapy Using a Light-Up Probe with Aggregation-Induced-Emission Characteristics. Angew. Chem. Inter. Ed. 2014, 53 (51), 14225-14229.
Wang, D.; Su, H.; Kwok, R. T.; Hu, X.; Zou, H.; Luo, Q.; Lee, M. M.; Xu, W.; Lam, J. W.; Tang, B. Z., Rational design of a water-soluble NIR AIEgen, and its application in ultrafast wash-free cellular imaging and photodynamic cancer cell ablation. Chem. Sci. 2018, 9 (15), 3685-3693.
Lou, X.; Zhang, M.; Zhao, Z.; Min, X.; Hakeem, A.; Huang, F.; Gao, P.; Xia, F.; Tang, B. Z., A photostable AIE fluorogen for lysosome-targetable imaging of living cells. J. Mater. Chem. B 2016, 4 (32), 5412-5417.
Dong Wang et al., Highly Efficient Photosensitizers with Far-Red/Near-Infrared Aggregation-Induced Emission for In Vitro and In Vivo Cancer Theranostics, Adv. Mater. 2018, 30, 1802105.
Anil Reddy Marri et al., Pyridinium p-DSSC dyes: An old acceptor learns new tricks, Dyes and Pigments 165 (2019) 508-517.
Miaomiao Kang et al., Evaluation of Structure—Function Relationships of Aggregation-Induced Emission Luminogens for Simultaneous Dual Applications of Specific Discrimination and Efficient Photodynamic Killing of Gram-Positive Bacteria, DOI: 10.1021/jacs.9b07162, J. Am. Chem. Soc. XXXX, XXX, XXX-XX.
First Office Action of CN2021100808297 issued from the China National Intellectual Property Administration dated Jan. 9, 2023.

* cited by examiner

*Primary Examiner* — Michael G. Hartley
*Assistant Examiner* — Leah H Schlientz
(74) *Attorney, Agent, or Firm* — S&F/WEHRW

(57) ABSTRACT

Provided herein are aggregation-induced emission luminogens useful as photodynamic therapy and imaging agents, compositions including two or more aggregation-induced emission luminogens, pharmaceutical compositions comprising the same, and methods of use and preparation thereof.

9 Claims, 18 Drawing Sheets

AGGREGATION-INDUCED EMISSION LUMINOGENS FOR PHOTODYNAMIC THERAPY

CROSS-REFERENCE TO RELATED APPLICATIONS

This application claims priority from U.S. Provisional Patent Application No. 62/995,270, filed on Jan. 22, 2020, which is incorporated herein by reference in its entirety.

TECHNICAL FIELD

The present disclosure relates to aggregation-induced emission luminogens (AIEgens) useful as targeted subcellular imaging and/or photodynamic therapy agents and pharmaceutical compositions comprising the same, and methods of use and preparation thereof.

BACKGROUND

Cancer, as a leading cause of death worldwide, has aroused great attention due to its limited early detection, rapid malignant progression, and late-stage metastasis. From global cancer statistics in 2018, there has been rapid growing trend of cancer incidence and mortality along with aging and socioeconomic development. Millions of people die of cancer each year, which is an alarming fact. In recent years, photodynamic therapy (PDT) has been discovered to induce apoptotic response of malignant cells through generation of radicals or reactive oxygen species (ROS) upon light irradiation. Since the first characterization of the photosensitizer hematoporphyrin derivative in 1960, PDT has been extensively explored to mediate tumor destruction. Compared with surgery, radiotherapy and chemotherapy, PDT is highly repeatable, of lower costs, less invasive, and rarely has long term side effects. So far, PDT has been highly recognized in clinical practice, appearing as a promising alternative therapeutic protocol for various types of cancers including skin, esophageal, lung, cervical, bladder, endobronchial, and even brain cancers.

Numerous photosensitizers have been developed thereby for clinical trials. However, conventional photosensitizers often possess certain drawbacks, such as poor photostability and chemical stability, low fluorescence quantum yield in aqueous media, insufficient penetration depth, small Stokes shift, and limited ROS generation ability. Moreover, some photosensitizers with extended π conjugation tend to be intrinsically planar in structure. This structural feature endows them with efficient luminescence in dilute solution but suppressed emission in aggregation state or in solid, which is commonly known as aggregation-caused quenching (ACQ). ACQ characteristics often hamper the practical applications of fluorescent photosensitizers, especially for fluorescence image-guided photodynamic therapy, which has been realized as one of the prominent modality of cancer theranostics. In this context, the emergence of photosensitizers with aggregation-induced emission (AIE) characteristics has triggered state-of-the-art development of cancer treatment. AIE luminogens (AIEgens) exhibit enhanced emission in aggregation state due to the principle of restriction of intramolecular motions (RIMs) that can block the nonradiative pathway upon aggregates formation. In addition, AIE photosensitizers also show boosted ROS generation efficiency in aggregation state through promoting intersystem crossing rate. As a result, a variety of AIEgens have been utilized as photosensitizers to carry out PDT application. Generally, an AIE photosensitizer is introduced inside cell to specifically target a type of subcellular organelle, and produce cytotoxic ROS upon light exposure that can destroy the subcellular functions. Some subcellular organelles including mitochondria, cellular membrane and lysosome, are wonderful cellular targeting sites for implementing PDT, because these subcellular organelles are closely related to various cellular processes and playing indispensable roles in manipulating cellular status.

Notwithstanding the great significance, PDT strategy is indeed undiversified and stereotyped in recent years. Scientists have spent a great deal of effort on developing novel photosensitizers, whereas PDT itself as a distinct strategy has been paid little attention and remains barely exploited. As we know that the issues of inefficient therapy and drug resistance could be elegantly addressed by drug synergism, in which equivalent therapeutic effect can be obtained with a much lower drug dose.

There thus exists a need for improved AIEgens useful as PDT theranostics that address or overcome the aforementioned challenges.

SUMMARY

Described herein is a strategy involving two or more AIEgens with a similar backbone were designed and used to specifically image mitochondria, cellular membrane and lysosome. As displayed by in vitro and in vivo PDT experiments, when ROS is generated from multiple areas inside cells, it can lead to more severe cell death and inhibit tumor growth to a larger extent at the same concentration of AIEgens.

Provided herein are two or more AIEgens that exhibit synergy in the ROS PDT of cancer cells. By structural tuning, these far-red/near-infrared luminogens with AIE features are capable of efficiently generating ROS, and specifically anchoring to different crucial organelles including mitochondria, cellular membrane and lysosome. Notably, both in vitro and in vivo studies demonstrate that by combined usage of two or more AIEgens, multiple ROS sources derived from different subcellular organelles exhibit significantly superior therapeutic effect than that of single organelle under the same photosensitizers' concentration.

In a first aspect, provided herein is an aggregation-induced emission luminogen (AIEgen) having the Formula 1:

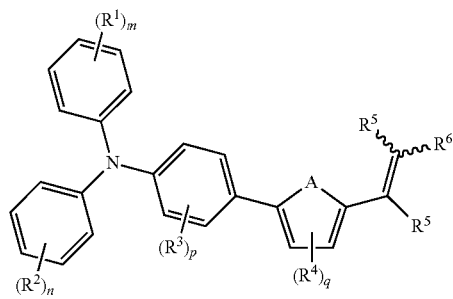

or a pharmaceutically acceptable salt thereof, wherein
A is O or S;
each of m and n is independently a whole number selected from 1-5;

p is a whole number selected from 1-4;
q is a whole number selected from 1-2;
r is a whole number selected from 2-6;
t for each occurrence is independently a whole number selected from 0-6;
u is a whole number selected from 1-4;
w for each occurrence is independently a whole number selected from 1-5;
each of $R^1$, $R^2$, $R^3$, and $R^4$ for each instance is independently selected from the group consisting of hydrogen, halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, $R^8$, and —$(CH_2)_tY$;
$R^5$ for each occurrence independently hydrogen or alkyl;
$R^6$ represents a moiety having structure:

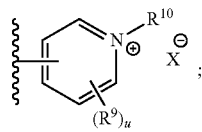

$R^7$ for each occurrence is independently selected from the group consisting of hydrogen, alkyl, cycloalkyl, alkenyl, alkynyl, aryl, aralkyl, heterocycloalkyl, and heteroaryl; or two instances of $R^7$ taken together with the atom or atoms to which they are covalently bonded form a 3-7 membered cycloalkyl or 3-7 membered heterocycloalkyl;
$R^8$ represents a moiety having the structure:

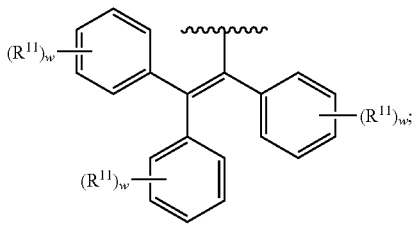

each of $R^9$ and $R^{11}$ for each instance is independently selected from the group consisting of hydrogen, halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, and —$(CH_2)_tY$;
$R^{10}$ is alkyl, cycloalkyl, alkenyl, alkynyl, aryl, aralkyl, heterocycloalkyl, heteroaryl, or —$(CH_2)_rN(R^{12})_3^+X^-$;
$R^{12}$ for each occurrence is independently alkyl, cycloalkyl, alkenyl, alkynyl, aryl, aralkyl, heterocycloalkyl, or heteroaryl; or two $R^{12}$ taken together with the nitrogen to which they are covalently bonded form a 3-7 membered heterocycloalkyl;
X for each occurrence is independently an anion; and
Y for each occurrence is independently selected from the group consisting of halide, —C≡CH, —$N_3$, —NCS, —NCO, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, and N-maleimide.

The AIEgen of claim 1, wherein each of m and n is independently 1 or 2; p is 1 or 2; q is 1 or 2; u is 1 or 2; and w is 1 or 2.

The AIEgen of claim 1, wherein each of m and n is 1; p is 1; q is 1; u is 1; and each $R^5$ is hydrogen.

The AIEgen of claim 3, wherein each of $R^1$ and $R^2$ is hydrogen; or
$R^1$ is independently selected from the group consisting of halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, $R^8$, and —$(CH_2)_tY$; and $R^2$ is hydrogen; or
$R^1$ is hydrogen; and $R^2$ is independently selected from the group consisting of halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, $R^8$, and —$(CH_2)_tY$; or
$R^1$ is $R^8$; and $R^2$ is independently selected from the group consisting of halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, and —$(CH_2)_tY$.

In certain embodiments, the AIEgen is represented by the Formula 2:

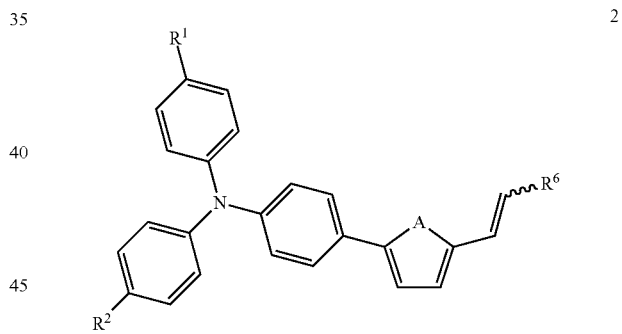

$R^6$ represents a moiety selected from the group consisting of:

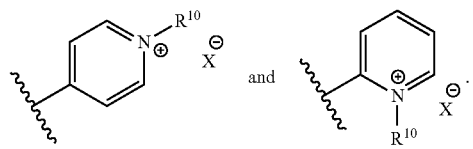

In certain embodiments, $R^{10}$ is alkyl, cycloalkyl, or —$(CH_2)_rN(R^{12})_3^+X^-$, wherein r is a whole number selected from 2-4.

In certain embodiments, $R^1$ is hydrogen, halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, $R^8$, or —$(CH_2)_tY$; and $R^2$ is hydrogen or a moiety is moiety having the structure:

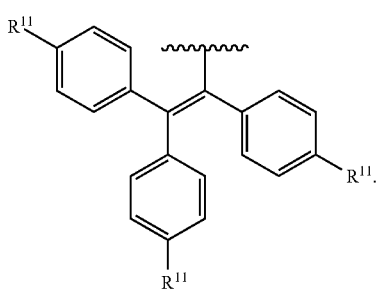

In certain embodiments, $R^{10}$ is alkyl.
In certain embodiments, A is O.
In certain embodiments, the AIEgen is represented by the Formula 3:

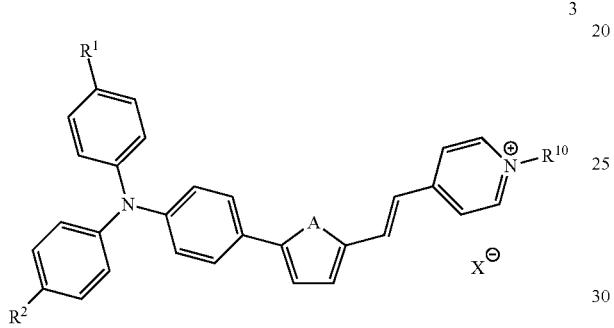

or a pharmaceutically salt thereof, wherein $R^1$ is hydrogen, halide, cyano, nitro, —$OR^7$, —$SR^7$, —$N(R^7)_2$, —(C=O)$R^7$, —(C=O)O$R^7$, —(C=O)N($R^7)_2$, —N($R^7$)(C=O)$R^7$, —O(C=O)$R^7$, —N($R^7$)(C=O)O$R^7$, —O(C=O)N($R^7)_2$, —$SO_2R^7$, —$SO_2N(R^7)_2$, alkyl, cycloalkyl, alkenyl, alkynyl, aryl, aralkyl, heterocycloalkyl, heteroaryl, $R^8$, or —(CH$_2$)$_t$Y; $R^2$ is hydrogen or a moiety is moiety having the structure:

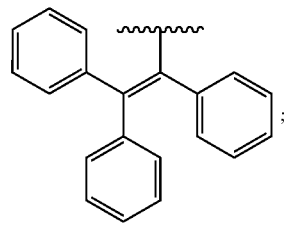 [SMILES: *C(=C(c1ccccc1)c1ccccc1)c1ccccc1]

and
$R^{10}$ is alkyl.
In certain embodiments, A is O; and $R^1$ is hydrogen or —(CH$_2$)$_t$Y.
In certain embodiments, the AIEgen is selected from the group consisting of:

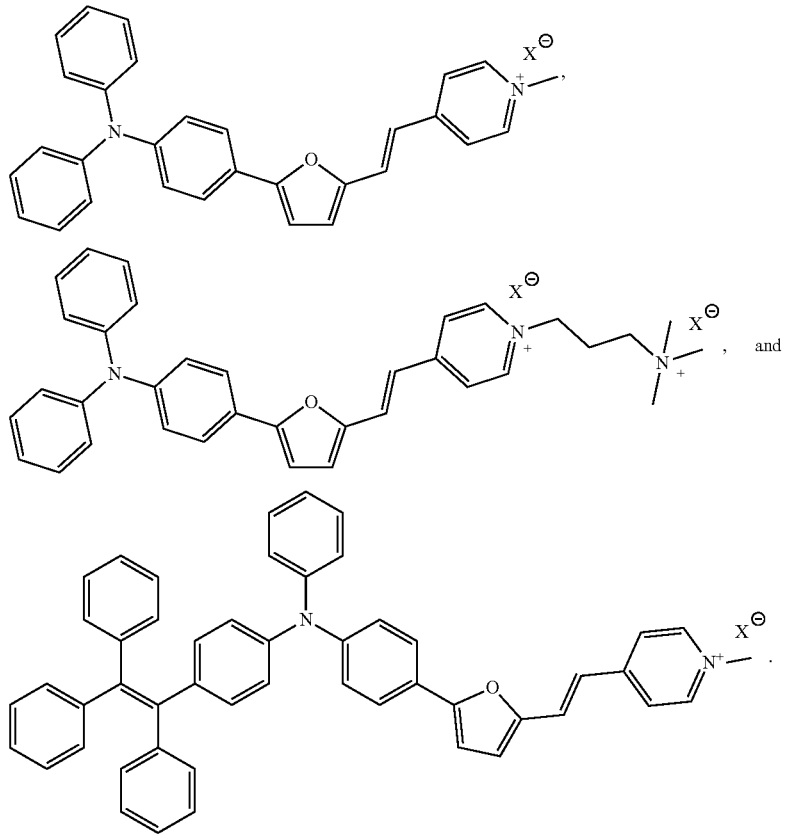

In a second aspect provided herein is a composition comprising two or more AIEgen.

In certain embodiments, the two or more AIEgen are:

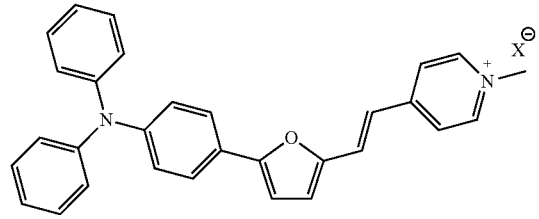 and

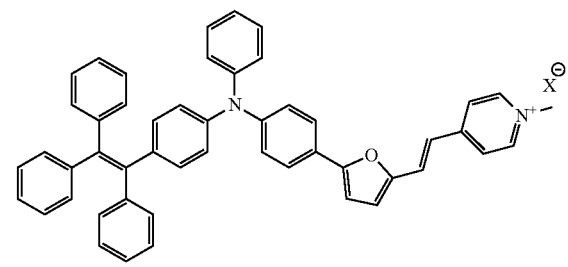

In certain embodiments, the composition further comprises:

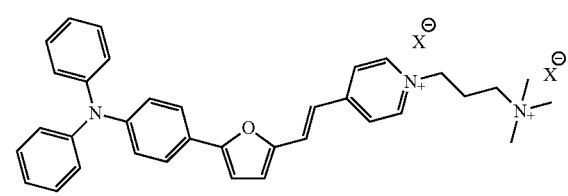

In a third aspect, provided herein is a pharmaceutical composition comprising at least one AIEgen and at least one pharmaceutically acceptable excipient.

In a fourth aspect, provided herein is a pharmaceutical composition comprising the comprising two or more AIEgen and at least one pharmaceutically acceptable excipient.

In a fifth aspect, provided herein is a method of treating a cancer cell, the method comprising: contacting the cancer cell with a therapeutically effective amount of at least one AIEgen; and irradiating the cancer cell with electromagnetic radiation in the presence of oxygen.

In a sixth aspect, provided herein is a method of imaging a cell, the method comprising: contacting the cell with at least one AIEgen; irradiating the cell with electromagnetic radiation; and detecting luminescence from the at least one AIEgen.

In a seventh aspect, provided herein is a method of preparing an AIEgen, the method comprising: contacting a compound having Formula 4:

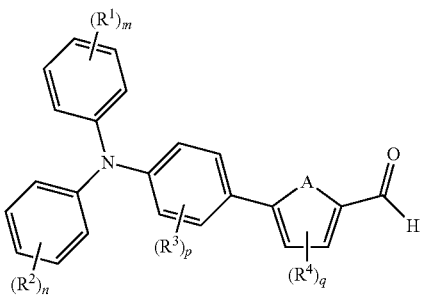

wherein
A is O or S;
each of m and n is independently a whole number selected from 0-5;
p is a whole number selected from 1-4;
q is a whole number selected from 1-2;
r is a whole number selected from 2-6;
t for each occurrence is independently a whole number selected from 0-6;
w for each occurrence is independently a whole number selected from 1-5;
each of $R^1$, $R^2$, $R^3$, and $R^4$ for each instance is independently selected from the group consisting of hydrogen, halide, cyano, nitro, $-OR^7$, $-SR^7$, $-N(R^7)_2$, $-(C=O)R^7$, $-(C=O)OR^7$, $-(C=O)N(R^7)_2$, $-N(R^7)(C=O)R^7$, $-O(C=O)R^7$, $-N(R^7)(C=O)OR^7$, $-O(C=O)N(R^7)_2$, $-SO_2R^7$, $-SO_2N(R^7)_2$, alkyl, cycloalkyl, alkenyl, alkynyl, aryl, aralkyl, heterocycloalkyl, heteroaryl, $R^8$, and $-(CH_2)_tY$;
$R^5$ for each occurrence independently hydrogen or alkyl;
$R^7$ for each occurrence is independently selected from the group consisting of hydrogen, alkyl, cycloalkyl, alkenyl, alkynyl, aryl, aralkyl, heterocycloalkyl, and heteroaryl; or two instances of $R^7$ taken together with the atom or atoms to which they are covalently bonded form a 3-7 membered cycloalkyl or 3-7 membered heterocycloalkyl;
$R^8$ represents a moiety having the structure:

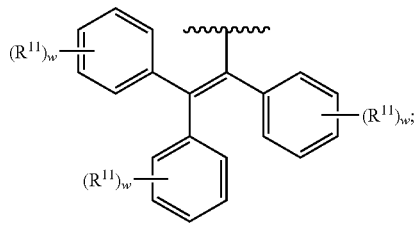

and
$R^{11}$ for each instance is independently selected from the group consisting of hydrogen, halide, cyano, nitro, $-OR^7$, $-SR^7$, $-N(R^7)_2$, $-(C=O)R^7$, $-(C=O)OR^7$, $-(C=O)N(R^7)_2$, $-N(R^7)(C=O)R^7$, $-O(C=O)R^7$, $-N(R^7)(C=O)OR^7$, $-O(C=O)N(R^7)_2$, $-SO_2R^7$, $-SO_2N(R^7)_2$, alkyl, cycloalkyl, alkenyl, alkynyl, aryl, aralkyl, heterocycloalkyl, heteroaryl, and $-(CH_2)_tY$;
with a secondary amine and a compound of Formula 5a or 5b:

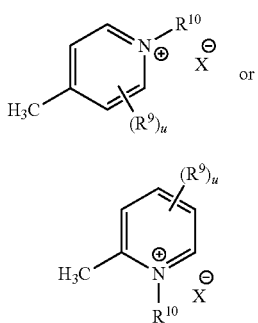

wherein u is a whole number selected from 1-4;

$R^9$ for each instance is independently selected from the group consisting of hydrogen, halide, cyano, nitro, —$OR^7$, —$SR^7$, —$N(R^7)_2$, —$(C=O)R^7$, —$(C=O)OR^7$, —$(C=O)N(R^7)_2$, —$N(R^7)(C=O)R^7$, —$O(C=O)R^7$, —$N(R^7)(C=O)OR^7$, —$O(C=O)N(R^7)_2$, —$SO_2R^7$, —$SO_2N(R^7)_2$, alkyl, cycloalkyl, alkenyl, alkynyl, aryl, aralkyl, heterocycloalkyl, heteroaryl, and —$(CH_2)_rY$; and $R^{10}$ is alkyl, cycloalkyl, alkenyl, alkynyl, aryl, aralkyl, heterocycloalkyl, heteroaryl, or —$(CH_2)_rN(R^{12})_3{}^+X^-$; and $R^{12}$ for each occurrence is independently alkyl, cycloalkyl, alkenyl, alkynyl, aryl, aralkyl, heterocycloalkyl, or heteroaryl; or two $R^{12}$ taken together with the nitrogen to which they are covalently bonded form a 3-7 membered heterocycloalkyl; thereby forming the AIEgen.

In certain embodiments, the AIEgens are used as selective bioimaging agents.

In certain embodiments, the AIEgens are used for cancer treatment through photodynamic therapy due to the reactive oxygen species generated by the far-red/NIR emissive molecule within cancer cells upon white light irradiation.

In certain embodiments, the AIEgens are used as bioimaging agents and photodynamic therapy agents.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present disclosure. It will be appreciated that these drawings depict exemplary embodiments of the invention and as such are not intended to limit its scope. The invention will be described and explained with additional specificity and detail through the use of the accompanying drawings.

DETAILED DESCRIPTION

Definitions

Figure 1:
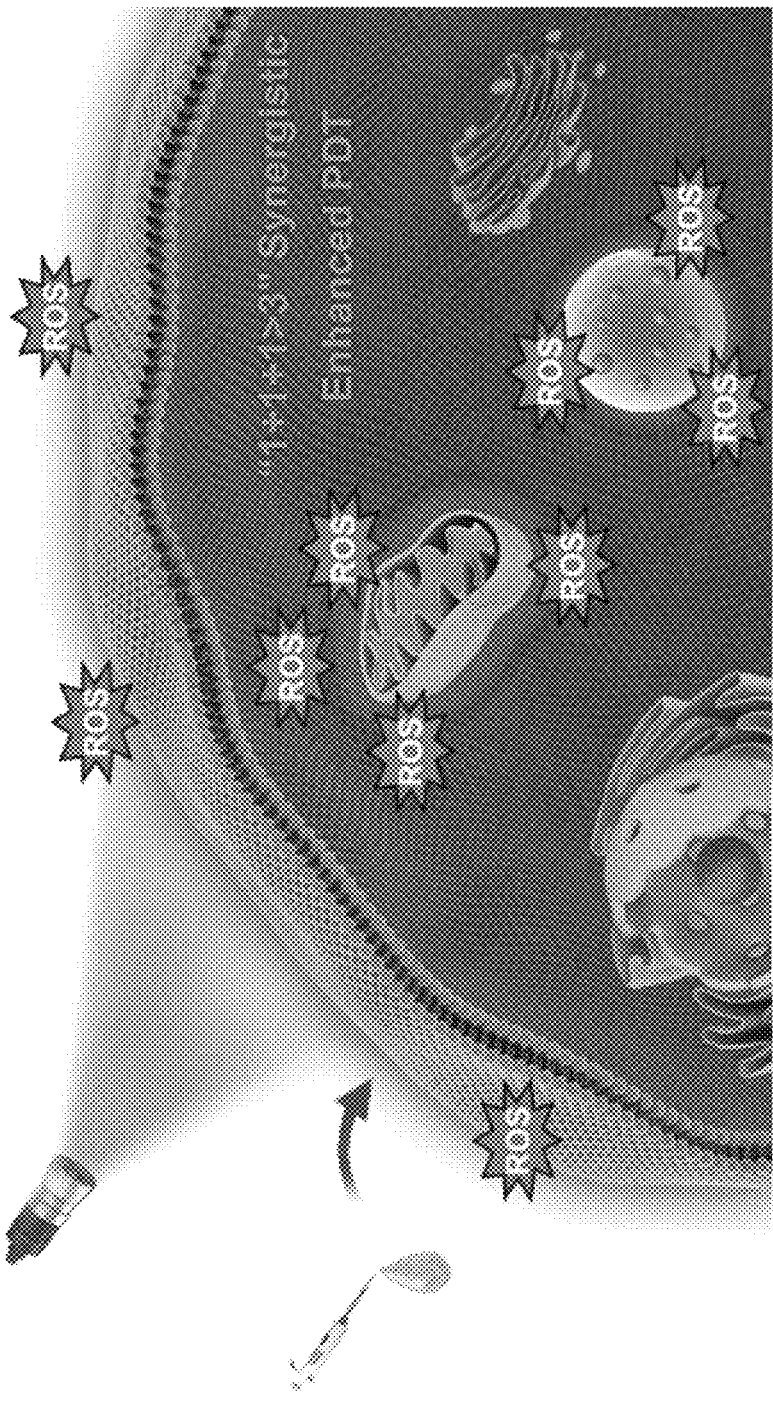
FIG. 1 depicts (A) chemical structures of three exemplary AIEgens: TFPy, TFVP and TPE-TFPy. (B) Schematic illustration of using three AIEgens for achieving "1+1+1>3" synergistic enhanced photodynamic therapy.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "halo", "halide", or "halogen" refers to fluoro, chloro, bromo, and iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., C1-40 alkyl group), for example, 1-30 carbon atoms (i.e., C1-30 alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

The term "aralkyl" is art-recognized and refers to an alkyl group substituted with an aryl group (e.g., an aromatic or heteroaromatic group).

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein. The aryl ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be optionally substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienooxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl, aryl, heteroaryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like The representation " " as used herein in connection to chemical a group or moiety is intended to represent the covalent bond that the aforementioned chemical group or moiety is covalently bonded to another chemical group or moiety.

The phrase "aggregation-induced emission" or "AIE" as used herein refers to the enhancement of light-emission by a fluorescent compound upon aggregation in the amorphous or crystalline (solid) states of the fluorescent compound, whereas the fluorescent compound exhibits weak or substantially no emission in dilute solutions.

The term "$\lambda_{ex}$" as used herein refers to the excitation wavelength.

The term "$\lambda_{em}$" as used herein refers to the emission wavelength.

As used herein by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "therapeutically effective" means the amount of the composition used is of sufficient quantity to ameliorate one or more causes or symptoms of a disease or disorder. Such amelioration only requires a reduction or alteration, not necessarily elimination.

As used herein, the term pharmaceutically acceptable salt refers to any salt of the compound of this invention which retains its biological properties and which is not toxic or otherwise undesirable for pharmaceutical use. Such salts may be derived from a variety of organic and inorganic counterions well known in the art and include them. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion (e.g., an alkali metal ion, an alkaline earth ion or an aluminum ion), or alkali metal or alkaline earth metal hydroxides (e.g., sodium, potassium, calcium, magnesium, aluminum, lithium, zinc, and barium hydroxide), ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. In addition, examples of salts include sodium, potassium, calcium, magnesium, ammonium, tetraalkylammonium and the like, and when the compound contains a basic functionality, salts of non-toxic organic or inorganic acids, such as hydrohalides (e.g., hydrochloride and hydrobromide), sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate; fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

When trade names are used herein, applicants intend to independently include the trade name product formulation, the generic drug, and the active pharmaceutical ingredient(s) of the trade name product.

Provided herein are AIEgen useful for PDT and/or imaging cancer cells. Advantageously, by the structure of the AIEgen can be designed to selectively bind different cellular organelles. In certain embodiments, the AIEgen has the Formula 1:

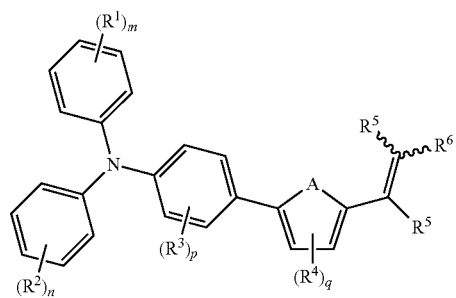

1 or a pharmaceutically acceptable salt thereof, wherein
A is O or S;
each of m and n is independently a whole number selected from 0-5;
p is a whole number selected from 1-4;
q is a whole number selected from 1-2;
r is a whole number selected from 2-6;
t for each occurrence is independently a whole number selected from 0-6;
u is a whole number selected from 1-4;
w for each occurrence is independently a whole number selected from 1-5;
each of $R^1$, $R^2$, $R^3$, and $R^4$ for each instance is independently selected from the group consisting of hydrogen, halide, cyano, nitro, $-OR^7$, $-SR^7$, $-N(R^7)_2$, $-(C=O)R^7$, $-(C=O)OR^7$, $-(C=O)N(R^7)_2$, $-N(R^7)(C=O)R^7$, $-O(C=O)R^7$, $-N(R^7)(C=O)OR^7$, $-O(C=O)N(R^7)_2$, $-SO_2R^7$, $-SO_2N(R^7)_2$, alkyl, cycloalkyl, alkenyl, alkynyl, aryl, aralkyl, heterocycloalkyl, heteroaryl, $R^8$, and $-(CH_2)_tY$;
$R^5$ for each occurrence independently hydrogen or alkyl;

$R^6$ represents a moiety having structure:

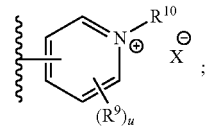

$R^7$ for each occurrence is independently selected from the group consisting of hydrogen, alkyl, cycloalkyl, alkenyl, alkynyl, aryl, aralkyl, heterocycloalkyl, and heteroaryl; or two instances of $R^7$ taken together with the atom or atoms to which they are covalently bonded form a 3-7 membered cycloalkyl or 3-7 membered heterocycloalkyl;
$R^8$ represents a moiety having the structure:

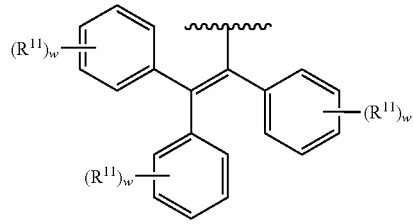

each of $R^9$ and $R^{11}$ for each instance is independently selected from the group consisting of hydrogen, halide, cyano, nitro, $-OR^7$, $-SR^7$, $-N(R^7)_2$, $-(C=O)R^7$, $-(C=O)OR^7$, $-(C=O)N(R^7)_2$, $-N(R^7)(C=O)R^7$, $-O(C=O)R^7$, $-N(R^7)(C=O)OR^7$, $-O(C=O)N(R^7)_2$, $-SO_2R^7$, $-SO_2N(R^7)_2$, alkyl, cycloalkyl, alkenyl, alkynyl, aryl, aralkyl, heterocycloalkyl, heteroaryl, and $-(CH_2)_tY$;
$R^{10}$ is alkyl, cycloalkyl, alkenyl, alkynyl, aryl, aralkyl, heterocycloalkyl, heteroaryl, or $-(CH_2)_rN(R^{12})_3{}^+X$;
$R^{12}$ for each occurrence is independently alkyl, cycloalkyl, alkenyl, alkynyl, aryl, aralkyl, heterocycloalkyl, or heteroaryl; or two $R^{12}$ taken together with the nitrogen to which they are covalently bonded form a 3-7 membered heterocycloalkyl;
X for each occurrence is independently an anion; and
Y for each occurrence is independently selected from the group consisting of $-C\equiv CH$, $-N_3$, $-NCS$, $-NCO$, $-OR^7$, $-SR^7$, $-N(R^7)_2$, $-(C=O)R^7$, $-(C=O)OR^7$, $-(C=O)N(R^7)_2$, $-N(R^7)(C=O)R^7$, $-O(C=O)R^7$, $-N(R^7)(C=O)OR^7$, $-O(C=O)N(R^7)_2$, $-SO_2R^7$, and $-SO_2N(R^7)_2$.

In certain embodiments, the AIEgen having Formula 1 does not comprise an AIEgen having the formula:

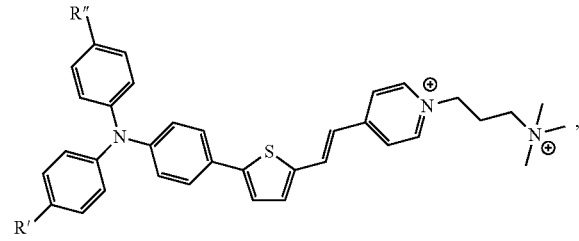

wherein each of R' and R" is independently selected from the group consisting of hydrogen, alkyl, alkenyl, alkynyl, heteroalkyl, heterocycloalkyl, aryl, heteroayl, alkyl-NCS, alkyl-$N_3$, and alkyl-$NH_2$; or R' is selected from the group consisting of hydrogen, alkyl, alkenyl, alkynyl, heteroalkyl, heterocycloalkyl, aryl, heteroayl, alkyl-NCS, alkyl-N$_3$, and alkyl-NH$_2$; and R" is moiety having the structure:

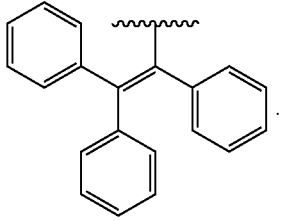 [SMILES: *C(=C(c1ccccc1)c1ccccc1)c1ccccc1]

In certain embodiments, the AIEgen having Formula 1 does not comprise an AIEgen comprising the formula:

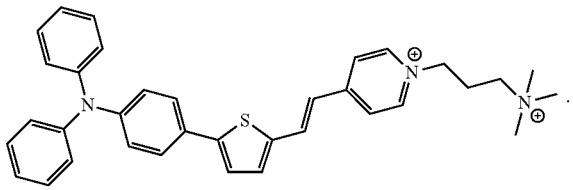 [SMILES: C[N+](C)(C)CCC[n+]1ccc(/C=C/c2ccc(-c3ccc(N(c4ccccc4)c4ccccc4)cc3)s2)cc1]

In certain embodiments, each of m and n are independently selected from 1-4, 1-3, 1-2, or 1.

In certain embodiments, p is 1-3, 1-2, or 1.

In certain embodiments, q is 1.

In certain embodiments, r is 2-5, 3-5, 2-4, or 2-3.

In certain embodiments, t is 1-6, 2-6, 2-5, 2-4, or 2-3.

In certain embodiments, u is 1-3, 1-2, or 1.

In certain embodiments, w is independently for each occurrence 1-4, 1-3, 1-2, or 1.

In certain embodiments, A is O.

In certain embodiments, each of $R^1$ and $R^2$ for each instance is independently selected from the group consisting of hydrogen, halide, —OR$^7$, —N(R$^7$)$_2$, —(C=O)OR$^7$, —(C=O)N(R$^7$)$_2$, —N(R$^7$)(C=O)R$^7$, —N(R$^7$)(C=O)OR$^7$, —O(C=O)N(R$^7$)$_2$, —SO$_2$N(R$^7$)$_2$, alkyl, cycloalkyl, alkenyl, alkynyl, aryl, aralkyl, heterocycloalkyl, heteroaryl, R$^8$, and —(CH$_2$)$_t$Y. In certain embodiments, each of $R^1$ and $R^2$ for each instance is independently selected from hydrogen, halide, —OR$^7$, —N(R$^7$)$_2$, aryl, heterocycloalkyl, heteroaryl, R$^8$, and —(CH$_2$)$_t$Y. In certain embodiments, each of $R^1$ and $R^2$ for each instance is independently selected from the group consisting of hydrogen, R$^8$, and —(CH$_2$)$_t$Y In certain embodiments, m and n are each 1; R$^1$ is R$^8$; and R$^2$ is hydrogen or —(CH$_2$)$_t$Y; or m and n are each 1; R$^1$ is hydrogen; and R$^2$ is hydrogen or —(CH$_2$)$_t$Y.

In certain embodiments, each of $R^3$ and $R^4$ for each instance is independently selected from the group consisting of hydrogen, halide, cyano, nitro, —OR$^7$, —N(R$^7$)$_2$, alkyl, cycloalkyl, alkenyl, alkynyl, aryl, aralkyl, heterocycloalkyl, and heteroaryl. In certain embodiments, each of $R^3$ and $R^4$ is hydrogen.

In certain embodiments, each $R^5$ is hydrogen.

In certain embodiments, $R^6$ is selected from the group consisting of:

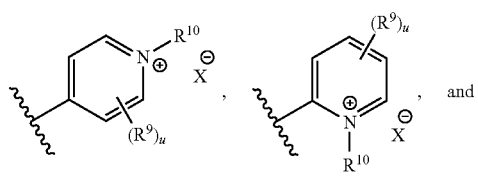

and

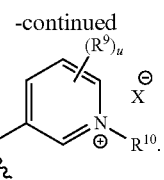

In certain embodiments, R$^7$ for each occurrence is independently selected from the group consisting of hydrogen, alkyl, cycloalkyl, aryl, aralkyl, heterocycloalkyl, and heteroaryl; or two instances of R$^7$ taken together with the atom or atoms to which they are covalently bonded form a 3-6 membered cycloalkyl or 3-6 membered heterocycloalkyl. In certain embodiments, R$^7$ for each occurrence is independently selected from the group consisting of hydrogen and alkyl.

In certain embodiments, R$^8$ is a moiety having the structure:

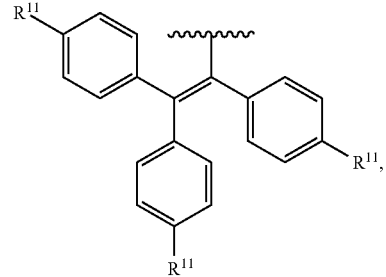

wherein R$^{11}$ for each instance independently selected from the group consisting of hydrogen, halide, cyano, nitro, —OR$^7$, —SR$^7$, —N(R$^7$)$_2$, —(C=O)R$^7$, —(C=O)OR$^7$, —(C=O)N(R$^7$)$_2$, —N(R$^7$)(C=O)R$^7$, —O(C=O)R$^7$, —N(R$^7$)(C=O)OR$^7$, —O(C=O)N (R$^7$)$_2$, —SO$_2$R$^7$, —SO$_2$N(R$^7$)$_2$, alkyl, cycloalkyl, alkenyl, alkynyl, aryl, aralkyl, heterocycloalkyl, heteroaryl, and —(CH$_2$)$_t$Y. In certain embodiments, each R$^{11}$ is hydrogen.

In certain embodiments, R$^9$ for each instance is independently selected from the group consisting of hydrogen, halide, cyano, nitro, —OR$^7$, —N(R$^7$)$_2$, alkyl, cycloalkyl, alkenyl, alkynyl, aryl, aralkyl, heterocycloalkyl, and heteroaryl. In certain embodiments, R$^9$ for each instance is hydrogen.

In certain embodiments, Y for each occurrence is selected from the group consisting of halide, —C≡CH, —N$_3$, —NCS, —NCO, —OH, —SH, —(C=O)H, —(C=O)OH, and N-maleimide.

In certain embodiments, R$^{10}$ is alkyl, cycloalkyl, aralkyl, or —(CH$_2$)$_r$N(R$^{12}$)$_3^+$X$^-$. In certain embodiments, R$^{10}$ is C$_1$-C$_{12}$ alkyl, C$_1$-C$_{10}$ alkyl, C$_1$-C$_8$ alkyl, C$_1$-C$_6$ alkyl, C$_1$-C$_4$ alkyl, C$_1$-C$_2$ alkyl, or —(CH$_2$)$_r$N(R$^{12}$)$_3^+$X$^-$, wherein r is 2-6, 2-4, 2-3, 3-4, or 3-5.

In certain embodiments, R$^{12}$ for each occurrence is independently C$_1$-C$_6$ alkyl, C$_1$-C$_4$ alkyl, or C$_1$-C$_2$ alkyl; or two R$^{12}$ taken together with the nitrogen to which they are covalently bonded form a 3-6 membered heterocycloalkyl.

X can be any anion known in the art. In certain embodiments, X for each instance is independently a pharmaceutically acceptable anion. Exemplary pharmaceutically acceptable anions, include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethylsuccinate, fumarate, gluceptate, gluconate, glutamate, glycollylarsanilate, hexylresorcinate, hydrabamine, bromide, chloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodide, and valerate salts. In certain embodiments, X for each instance is independently pentafluorophosphate or tetrafluoroborate.

It has been surprisingly discovered that the AIEgen of Formula 1 are capable of selectively binding specific organelles found in cells, which make the AIEgen described herein useful as organelle selective imaging and/or PDT agents. In certain embodiments, the cell is a mammalian cell. In certain embodiments, the cell is a cancer cell.

Compounds having Formula 6 have been shown to selectively bind to mitochondria:

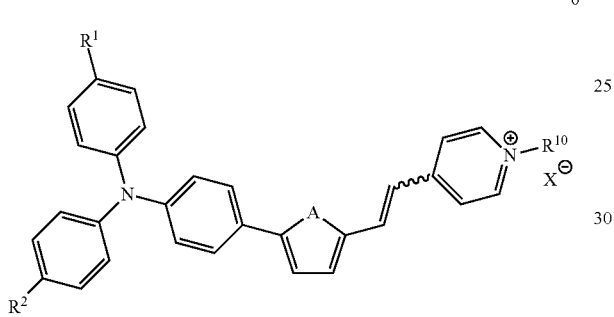

6 wherein $R^{10}$ is alkyl; and A, $R^1$, $R^2$, and X are as defined in any one or more embodiments described herein with the proviso that $R^1$ and $R^2$ cannot be $R^8$. In certain embodiments of the AIEgen of Formula 6, A is O or S; X is an anion; $R^1$ is hydrogen; $R^2$ is hydrogen or —(CH$_2$)$_r$Y; and $R^{10}$ is alkyl. In certain embodiments of the AIEgen of Formula 6, A is O; X is a pharmaceutically acceptable anion; $R^1$ is hydrogen; $R^2$ is hydrogen and $R^{10}$ is methyl.

Compounds having Formula 7 have been shown to selectively bind to lysosome:

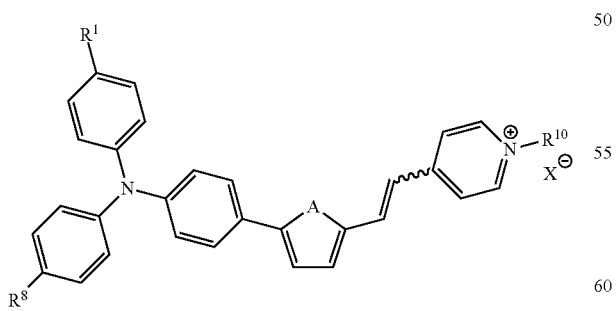

7 wherein $R^{10}$ is alkyl; and A, $R^1$, $R^8$, and X are as defined in any one or more embodiments described herein. In certain embodiments of the AIEgen of Formula 6, A is O or S; X is an anion; $R^1$ is hydrogen or —(CH$_2$)$_r$Y; $R^{10}$ is alkyl; and $R^8$ is a moiety having the formula:

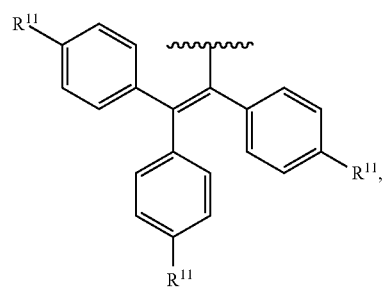

wherein $R^{11}$ for each instance is independently as defined in any one or more embodiments described herein. In certain embodiments of the AIEgen of Formula 7, A is O; X is a pharmaceutically acceptable anion; $R^1$ is hydrogen; $R^{10}$ is methyl; and $R^8$ is a moiety having the formula:

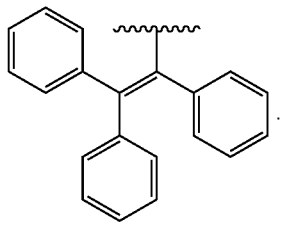

Compounds having Formula 8 have been shown to selectively bind to the cell membrane:

8

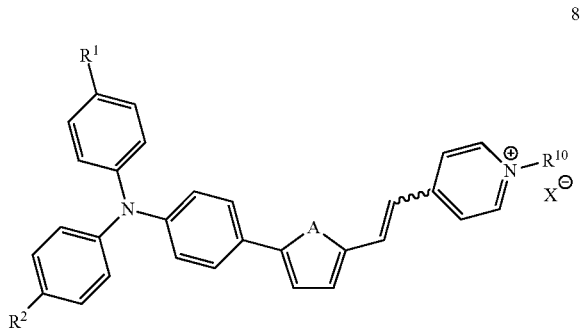

wherein $R^{10}$ is —(CH$_2$)$_r$N(R$^{12}$)$_3^+$X$^-$; and A, $R^1$, $R^8$, and X are as defined in any one or more embodiments described herein. In certain embodiments of the AIEgen of Formula 8, A is O; X is a pharmaceutically acceptable anion; $R^1$ is hydrogen or —(CH$_2$)$_r$Y; $R^2$ is hydrogen or $R^8$; and $R^{10}$ is —(CH$_2$)$_r$N(R$^{12}$)$_3^+$X$^-$, wherein r is a whole number selected from 2-5; and $R^{12}$ is $C_1$-$C_6$ alkyl. In certain embodiments of the AIEgen of Formula 8, A is O; X is a pharmaceutically acceptable anion; $R^1$ is hydrogen; $R^2$ is hydrogen; and $R^{10}$ is —(CH$_2$)$_3$N(Me)$_3^+$X$^-$.

The present disclosure also provides a pharmaceutical composition comprising at least one of the AIEgen described herein and at least one pharmaceutically acceptable excipient.

The AIEgen described herein and their pharmaceutically acceptable salts can be administered to a subject either alone or in combination with pharmaceutically acceptable, excipients, carriers, and/or diluents in a pharmaceutical composition according to standard pharmaceutical practice. The AIEgen can be administered orally or parenterally. Parenteral administration includes intravenous, intramuscular, intraperitoneal, subcutaneous and topical, the preferred method being intravenous and topical administrations.

Accordingly, the present disclosure provides pharmaceutically acceptable compositions, which comprise a therapeutically effective amount of one or more of the AIEgen described herein, formulated together with one or more pharmaceutically, excipients, acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the AIEgen described herein may contain a basic functional group, such as amino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of AIEgen of the present disclosure. These salts can be prepared in situ in the administration vehicle or the dosage form manufacturing process, or by separately reacting a purified AIEgen of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like.

The pharmaceutically acceptable salts of the AIEgen of the present disclosure include the conventional non-toxic salts or quaternary ammonium salts of the AIEgen, e.g., from non-toxic organic or inorganic acids. For example, such conventional non-toxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the AIEgen described herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of AIEgen of the present disclosure. These salts can likewise be prepared in situ in the administration vehicle or the dosage form manufacturing process, or by separately reacting the purified AIEgen in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations include the step of bringing into association a AIEgen described herein with the carrier or excipient and, optionally, one or more accessory ingredients. In general, the formulations are prepared by uniformly and intimately bringing into association a AIEgen of the present disclosure with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more AIEgen described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the AIEgen of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Also provided herein is a method for preparing an AIEgen having Formula 1, the method comprising: contacting a compound having Formula 4:

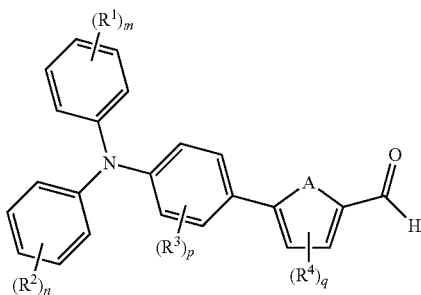

4

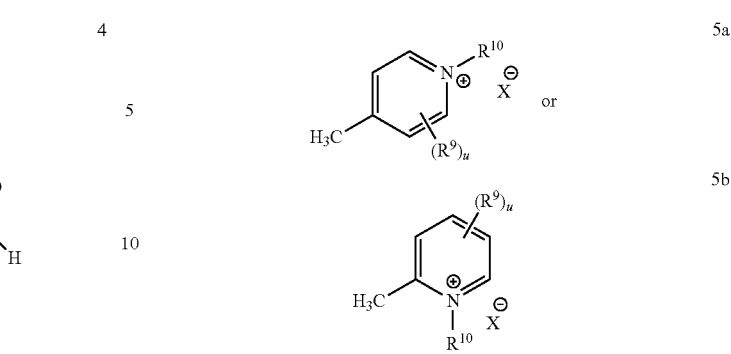

5a

5b wherein

A is O or S;

each of m and n is independently a whole number selected from 0-5;

p is a whole number selected from 1-4;

q is a whole number selected from 1-2;

r is a whole number selected from 2-6;

t for each occurrence is independently a whole number selected from 0-6;

w for each occurrence is independently a whole number selected from 1-5;

each of $R^1$, $R^2$, $R^3$, and $R^4$ for each instance is independently selected from the group consisting of hydrogen, halide, cyano, nitro, —$OR^7$, —$SR^7$, —$N(R^7)_2$, —(C=O)$R^7$, —(C=O)O$R^7$, —(C=O)N($R^7$)$_2$, —N($R^7$)(C=O)$R^7$, —O(C=O)$R^7$, —N($R^7$)(C=O)O$R^7$, —O(C=O)N($R^7$)$_2$, —$SO_2R^7$, —$SO_2N(R^7)_2$, alkyl, cycloalkyl, alkenyl, alkynyl, aryl, aralkyl, heterocycloalkyl, heteroaryl, $R^8$, and —(CH$_2$)$_t$Y;

$R^5$ for each occurrence independently hydrogen or alkyl;

$R^7$ for each occurrence is independently selected from the group consisting of hydrogen, alkyl, cycloalkyl, alkenyl, alkynyl, aryl, aralkyl, heterocycloalkyl, and heteroaryl; or two instances of $R^7$ taken together with the atom or atoms to which they are covalently bonded form a 3-7 membered cycloalkyl or 3-7 membered heterocycloalkyl;

$R^8$ represents a moiety having the structure:

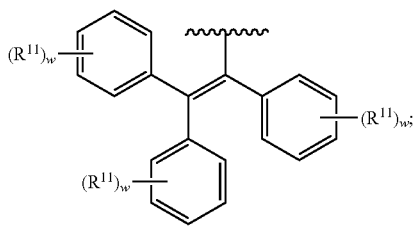

and $R^{11}$ for each instance is independently selected from the group consisting of hydrogen, halide, cyano, nitro, —$OR^7$, —$SR^7$, —$N(R^7)_2$, —(C=O)$R^7$, —(C=O)O$R^7$, —(C=O)N($R^7$)$_2$, —N($R^7$)(C=O)$R^7$, —O(C=O)$R^7$, —N($R^7$)(C=O)O$R^7$, —O(C=O)N($R^7$)$_2$, —$SO_2R^7$, —$SO_2N(R^7)_2$, alkyl, cycloalkyl, alkenyl, alkynyl, aryl, aralkyl, heterocycloalkyl, heteroaryl, and —(CH$_2$)$_t$Y;

with a secondary amine and a compound of Formula 5a or 5b:

or a conjugate base thereof, wherein u is a whole number selected from 1-4;

$R^9$ for each instance is independently selected from the group consisting of hydrogen, halide, cyano, nitro, —$OR^7$, —$SR^7$, —$N(R^7)_2$, —(C=O)$R^7$, —(C=O)O$R^7$, —(C=O)N($R^7$)$_2$, —N($R^7$)(C=O)$R^7$, —O(C=O)$R^7$, —N($R^7$)(C=O)O$R^7$, —O(C=O)N($R^7$)$_2$, —$SO_2R^7$, —$SO_2N(R^7)_2$, alkyl, cycloalkyl, alkenyl, alkynyl, aryl, aralkyl, heterocycloalkyl, heteroaryl, and —(CH$_2$)$_t$Y; and $R^{10}$ is alkyl, cycloalkyl, alkenyl, alkynyl, aryl, aralkyl, heterocycloalkyl, heteroaryl, or —(CH$_2$)$_r$N($R^{12}$)$_3^+$X$^-$; and $R^{12}$ for each occurrence is independently alkyl, cycloalkyl, alkenyl, alkynyl, aryl, aralkyl, heterocycloalkyl, or heteroaryl; or two $R^{12}$ taken together with the nitrogen to which they are covalently bonded form a 3-7 membered heterocycloalkyl; thereby forming the AIEgen having Formula 1.

Any secondary amine can be used in the method for preparing the AIEgen having Formula 1. The selection of a suitable secondary amine is well within the skin of a person of ordinary skill in the art. In certain embodiments, the dialkylamine has the formula HN($R^{13}$)$_2$, wherein $R^{13}$ for each occurrence is independently alkyl, cycloalkyl, or heterocycloalkyl; or two instances of $R^{13}$ taken together form 5-6 membered heterocycloalkyl comprising heteroatoms selected from O, N, and S. Exemplary secondary amines include, but are not limited to dialkyl amines, such as dimethylamine, diethyl amine, morpholine, piperazine piperidine, pyrrolidine, and the like.

The compound of Formula 4, the secondary amine, and the compound of Formula 5a or 5b can be contacted in any order. In certain embodiments, all or some of reagents are added substantially at the same time, added sequentially, or a combination thereof. In certain embodiments, the secondary amine is brought into contact with the compound of Formula 4 and then the compound of Formula 5a or 5b is brought in to contact. In other embodiments, the compound of Formula 4 is brought in to contact with the compound of Formula 5a or 5b and then the secondary amine is brought in to contact.

The preparation of the AIEgen having Formula 1 can be conducted in any solvent, conducted neat, or conducted using the secondary amine as the solvent. Exemplary solvents include polar solvents, such as water, polar protic organic solvents, polar aprotic organic solvents, and mixtures thereof. Exemplary solvents include, but are not limited to, alcohols, ketones, formamides, haloalkanes, aromatic solvents, ethers, dialkylsulfoxides, and mixtures thereof. In certain embodiments, the solvent is methanol, ethanol, 1-propanol, 2-propanol, or a mixture thereof.

The preparation of the AIEgen having Formula 1 can be conducted at a temperature between 23-120° C. In certain embodiments, the preparation of the AIEgen having Formula 1 can is conducted at a temperature 23-100° C., 23-90° C., 30-90° C., 40-90° C., 50-120° C., 60-90° C., 70-90° C., or 70-80° C.

The present disclosure also provides a method of treating a cancer, the method comprising: contacting the cancer cell with a therapeutically effective amount of at least one AIEgen described herein; and irradiating the cancer cell with electromagnetic radiation in the presence of oxygen.

In certain embodiments, the cancer is irradiated with white light.

In certain embodiments the cancer is contacted with 1, 2, 3, or more AIEgen described herein.

The method of treating a cancer may be conducted in vivo, in vitro, or ex vivo. In instances in which the method of treating cancer occurs in vivo, a therapeutically effective amount of at least one AIEgen described herein can be administered to a subject, the site of the cancer in the subject can then be irradiated with electromagnetic radiation in the presence of oxygen. The subject may be a mammal, The cancer can be a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

The present disclosure also provides a method of imaging a cell, the method comprising: contacting the cell with at least one AIEgen described herein; irradiating the cell with electromagnetic radiation; and detecting luminescence from the AIEgen.

The cell may be any mammalian cell. In certain embodiments, the cell is a cancer cell.

The cancer cell may be derived from a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In certain embodiments, the cancer cell is HeLa or 4T1.

The AIEgen may be selective for certain organelles in the cell. In certain embodiment, the AIEgen may selectively bind to the cell membrane, the mitochondria, or the lysosome, which allows selective imaging of the aforementioned organelles.

In certain embodiments the cell is contacted with 1, 2, 3, or more AIEgen described herein.

The electromagnetic radiation may have an absorption wavelength $\lambda_{abs}$ between 400-600 nm, 450-550 nm, 450-525 nm, 450-500 nm, 470-500 nm, or 480-500 nm.

The luminescence may have an emission wavelength $\lambda_{em}$ between 600-750 nm, 600-700 nm, 650-700 nm, or 660-690 nm.

Having described the invention, the following examples are given to illustrate specific applications of the invention including the best mode now known to perform the invention. These specific examples are not intended to limit the scope of the invention described in this application.

Experimental Section

Materials and Methods

All the chemicals were purchased from Meryer, J&K, or Sigma as received without further purification. Superdry (99.9%) DCM and methanol with molecular sieves were purchased from J&K Scientific. Toluene was distilled from sodium and benzophenone under nitrogen prior to use. Phosphate buffered saline (PBS) was purchased from Thermo Fisher Scientific. ABDA, Ce6 and Rose Bengal were purchased from Sigma-Aldrich and used as received. Cell culture medium and fetal bovine serum (FBS) were purchased from GIBCO (Gran Island, NY, USA). Mitotracker Green, CellMask Green, and LysoTracker Green were purchased from ThermoFisherScientific. 1H NMR (400 MHz), 13C NMR (100 MHz) spectra were recorded on a Bruker ARX 400 Spectrometer with $CDCl_3$ or $d_6$-DMSO as deuterated solvent. High resolution mass spectra (HRMS) were performed on a Finnigan MAT TAQ 7000 mass spectrometer system operating in matrix-assisted laser desorption/ionization time of flight mass spectrometry (MALDI-TOF) mode. UV-Vis absorption and fluorescence spectra were recorded with Milton Roy Spectronic 3000 array spectrophotometer. Fluorescence images of AIEgens in solution and aggregation state were collected on an Olympus BX 41 fluorescence microscope. Cellular fluorescence images were taken using a Zeiss laser scanning confocal microscope (LSM7 DUO) and analyzed using ZEN 2009 software (Carl Zeiss). Theoretical study was carried out on 6-311G* basis set in Gaussian09 using density functional theory (DFT) approximated by ωB97X-D.

ROS Generation Measurement 9,10-Anthracenediyl-bis(methylene)dimalonic acid (ABDA) was employed to detect ROS generation of TFPy, TFVP, TPE-TFPy, and two commercial standard photosensitizer, Rose Bengal, and Ce6 upon light irradiation. The absorbance of each sample (1 μM) was firstly set as blank. Then, 10 μM of ABDA was mixed to each sample (DMSO/water (v:v)=1/100) in a dark room, and the absorbance of sample was measured at once. The sample mixture was then irradiated under white light (4.2 mW/cm$^{-2}$) at intervals of 1 min until 6 min. The absorption of ABDA at 378 nm was recorded at various irradiation times to obtain the decay rate of photosensitizing process. The absorbance change of ABDA alone in 6 min light irradiation time was also measured as control.

Hela Cell Imaging

Hela cells were seeded and cultured at 37° C. in a 35 mm glass-bottomed dish. After incubation with TFPy (1 μM), TFVP (5 μM), or TPE-TFPy (2 μM), the cells were washed with PBS three times and subjected to imaging analysis using a Zeiss Laser Scanning Confocal Microscope. All of three AIEgens can be excited with 488 nm filter and the emission filter was 570-740 nm. For co-staining assay, the TFPy, TFVP, and TPE-TFPy loaded Hela cells were subjected to incubation with MitoTracker Green, CellMask Green, and LysoTracker Green, respectively. Hoechst 33258 (5 μM) was also utilized to stain nuclear DNA to assist visualizing. Afterwards, the cells were washed with PBS and then observed with CLSM. The cells were imaged using appropriate excitation and emission filters for each dye. The co-localization efficiency was analyzed with Olympus FV10-ASW software, in which the calculated Pearson's coefficient was 0.90 for TFPy, 0.91 for TFVP, and 0.90 for TPE-TFPy. A stock solution of three AIEgens comprising of 1 μM TFPy, 10 μM TFVP, and 1 μM TPE-TFPy was utilized to incubate with Hela cells, followed by imaging analysis excited with 488 nm filter.

4T1 Cell Imaging

Similar co-staining procedure for Hela cell was applied on 4T1 cell. The calculated Pearson's coefficient was 0.90 for TFPy, 0.91 for TFVP, and 0.90 for TPE-TFPy.

Photostability

For photostability assay, cells were imaged using a Zeiss Laser Scanning Confocal Microscope and analyzed using ZEN 2009 software (Carl Zeiss). Both TFPy and MitoTracker Green were excited at 488 nm (0.6% laser power). Both TFVP and CellMask Green were excited at 488 nm (0.7% laser power). TPE-TFPy was excited at 488 nm, whereas LysoTracker Green was excited at 514 nm with 1% laser power. The scanning speed was 22.4 s per scan, and the repeated image scans were taken 40 times. The first scan of all the presented photosensitizers were set to 100%, followed by which the pixel intensity values were averaged and plotted against the scan number. The resulting curve represents the photobleaching rate.

Cytotoxicity Assay 3-(4,5-Dimethylthiazol-2-yl)-2,5-diphenyltetrazolium bromide (MTT) assay was utilized to quantitatively measure the cytotoxicity of TFPy, TFVP, TPE-TFPy, and three in one group based on both Hela cell line and 4T1 cell line. The three in one group was consist of one third concentration of TFPy, TFVP, and TPE-TFPY. Both cancer cell lines were seeded in DMEM media in a 96-well round-bottom microplate with a density of $1 \times 10^4$ cells per well. The AIEgens (TFPy, TFVP, TPE-TFPy, and three in one) were added at different concentrations of 0, 0.25, 0.5, 1, 2.5, and 5 μM after replacing the medium, and was incubated with different cell lines respectively for 20 min, followed by irradiation with white light for 20 min (20 mW/cm$^2$); and another array of plates with cells were kept in the dark as control. After 24 h incubation, 10 uL MTT (5 mg/mL in PBS) was added into each well. 4 hours later, DMSO was added into wells to dissolve the precipitated formazan. Finally, the absorption of each well at 595 nm was recorded via a plate reader (Perkin-Elmer Victor3™). Each trial was performed with 6 wells in parallel.

Animal Model

All animal procedures were performed in accordance with the Guidelines for Care and Use of Laboratory Animals of Chinese Academy of Medical Sciences (CAMS) and Peking Union Medical College, and approved by the Animal Ethics Committee of CAMS and Peking Union Medical College. Tumor-bearing mice were prepared by subcutaneously injection of 100 uL of $1 \times 10^6$ 4T1 single-cell suspension in PBS into the back of nude mice. After 10 days, the mice bearing 4T1 tumors with an average volume of ~100 mm$^3$ were administered with TFPy, TFVP, TPE-TFPy, and three in one experimental group by intratumor injection of PDT measurement.

In Vivo PDT Assay

4T1 Tumor-bearing mice were randomly divided into five groups with the same number of male and female, and treated by intratumor injection of 100 uL PBS (control group), TFPy (10 mg/mL), TFVP (10 mg/mL), TPE-TFPy (10 mg/mL), and three in one group containing TFPy (10/3 mg/mL)+TFVP (10/3 mg/mL)+TPE-TFPy (10/3 mg/mL), respectively. Four hours later, mice were irradiated with white light (100 mW/cm$^2$) for 10 min. The treatments were conducted every three days. Tumor volumes and tumor weights of mice were recorded every three days accordingly. The tumor volume was calculated as: (tumor length×(tumor width)2)/2. The relative tumor growth ratio was reflected by the relative volume V/V$_0$ (V$_0$ as the initial tumor volume before treatment). All mice were euthanized 15 days after first injection. The tumors were then weighed and dissected, prior to H&E analysis.

Histology Examination

After tumor-bearing mice were sacrificed, tumor, heart, liver, spleen, lung, and kidney were taken out for histological analysis. The collected tissues were fixed in 4% paraformaldehyde for the histological analysis, and then embedded in paraffin. The fixed tissues were cut into slices with a thickness of 4 mm. Thereafter, H&E staining was carried out according to the standard protocols as described in the previous work. The morphology of tumor tissues was observed using a Leica DM IL LED inverted phase contrast microscope.

Synthesis

Both TFPy and TFVP are synthesized based on 5-(4-(diphenylamino)phenyl)furan-2-carbaldehyde intermediate. Scheme 1 depicts an exemplary synthetic route to TFPy and TFVP.

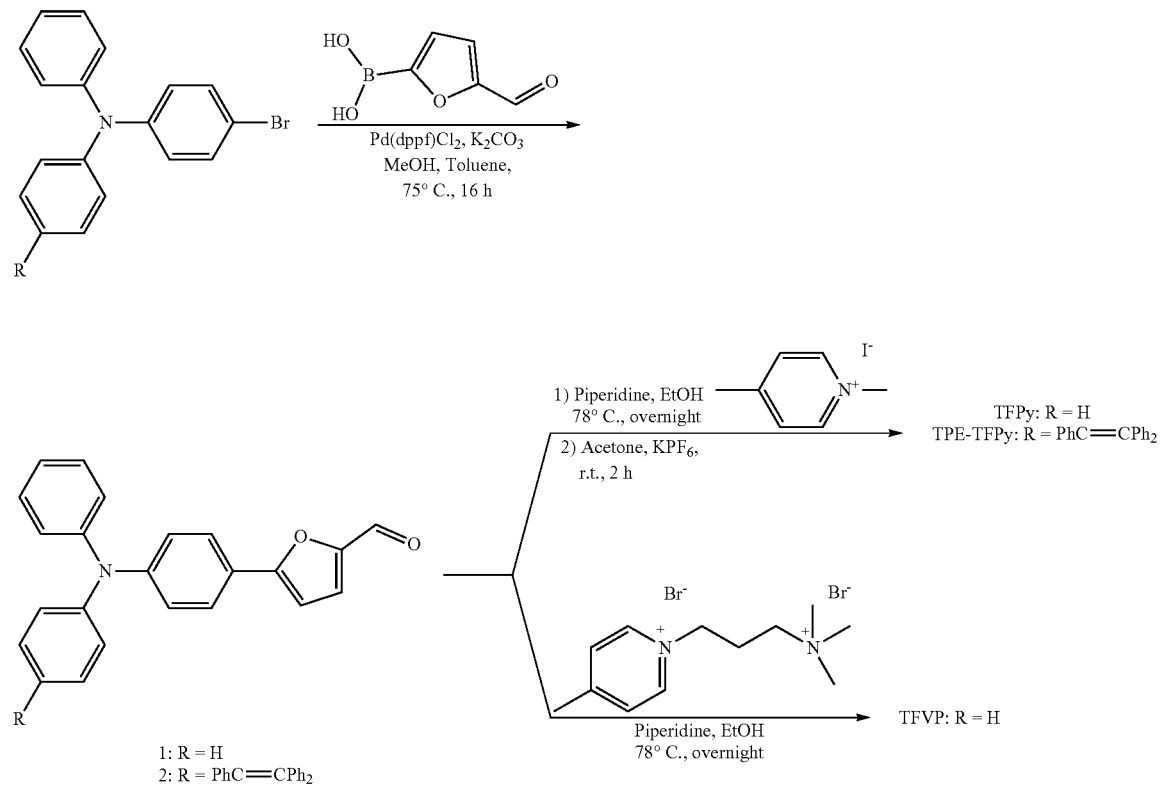

Example 1—Synthesis of TFPy

Synthesis of compound 5-(4-(diphenylamino)phenyl)furan-2-carbaldehyde (1): A mixture of 4-bromo-N,N-diphenylaniline (1.0 mol), (5-formylfuran-2-yl)boronic acid (2.0 mol), Pd(dppf)Cl$_2$ (0.1 mol) and K$_2$CO$_3$ (3 mol) were dissolved in mixed solvent (MeOH:Toluene=3:3 mL). The reaction was heated to 75° C. for 16 h under nitrogen. When the reaction was completed, the mixture was cooled to room temperature and filtered, of which the solvent was removed by reduced pressure. The residue was dissolved in DCM (100 mL) and washed by water (50 mL×3). The combined organic phase was dried over Na$_2$SO$_4$ and filtered; the filtrate was removed under reduced pressure in order to obtain the crude product, which was further purified by silica gel chromatography (Hex:EtOAc=10:1) to give product with the yield of 70%. $^1$H-NMR (400 MHz, CDCl$_3$, δ): 9.59 (s, 1H), 7.66 (d, 2H, J=9.0 Hz), 7.32-7.27 (m, 5H), 7.15-7.06 (m, 8H), 6.71 (d, 1H, J=3.7 Hz).

Synthesis of compound TFPy: A mixture of 5-(4-(diphenylamino)phenyl)furan-2-carbaldehyde (1) (0.2 mol) and 1,4-Dimethylpyridinium iodide (0.2 mol) was refluxed in ethanol (2 mL) overnight under the catalysis of a few drops of piperidine. After cooling down to room temperature, the solvent was removed and the residue was dissolved and stirred in mixed solvent (Acetone:KPF$_6$=5:5 mL) for 30 min. Then the resultant mixture was purified by chromatography using DCM/MeOH as eluents to afford TFPy (82.6 mg) as red solid in 72% yield. $^1$H NMR (400 MHz, Chloroform-d) δ 8.89 (d, J=6.5 Hz, 2H), 7.87 (d, J=6.5 Hz, 2H), 7.62-7.57 (m, 2H), 7.49 (d, J=15.7 Hz, 1H), 7.33-7.27 (m, 4H), 7.16-7.05 (m, 8H), 6.97-6.91 (m, 2H), 6.67 (d, J=3.6 Hz, 1H), 4.49 (s, 3H). $^{13}$C NMR (100 MHz, DMSO-d$_6$) δ 156.11, 150.56, 147.78, 146.54, 144.73, 129.73, 127.03, 125.64, 124.69, 123.89, 122.88, 122.71, 122.07, 119.55, 119.08, 108.26, 46.69. ESI HRMS: calcd. for C$_{30}$H$_{25}$N$_2$O$^+$ [M−PF$_6$]$^+$: 429.1961, found: 429.1950.

Example 2—Synthesis of TFVP is Based on Compound 5-(4-(diphenylamino)phenyl)furan-2-carbaldehyde (1)

A mixture of 5-(4-(diphenylamino)phenyl)furan-2-carbaldehyde (1) (0.2 mol) and Pyridinium, 4-methyl-1-[3-(trimethylammonio)propyl]-, dibromide (0.2 mol) was refluxed in ethanol (2 mL) for 24 h under the catalysis of a few drops of piperidine. After cooling down to room temperature, the solvent was removed by reduced pressure. The residue was purified by chromatography using DCM/MeOH as eluents to afford TFVP (89 mg) as dark red solid in 66% yield. $^1$H NMR (400 MHz, DMSO-d$_6$) δ 8.90 (d, J=6.5 Hz, 2H), 8.24 (d, J=6.4 Hz, 2H), 7.94 (d, J=15.9 Hz, 1H), 7.77 (d, J=8.5 Hz, 2H), 7.36 (t, J=7.7 Hz, 4H), 7.27 (d, J=15.9 Hz, 1H), 7.16-7.05 (m, 8H), 7.02 (d, J=8.5 Hz, 2H), 4.53 (t, J=7.4 Hz, 2H), 3.40 (d, J=9.9 Hz, 2H), 3.08 (s, 9H), 2.42 (s, 2H). $^{13}$C NMR (100 MHz, DMSO-d$_6$) δ 156.36, 150.57, 147.90, 146.53, 144.07, 129.76, 127.53, 125.71, 124.74, 123.96, 123.21, 122.62, 122.03, 119.53, 119.45, 108.40, 61.83, 56.41, 52.50, 24.05.

Example 3—Syntheses of TPE-TFPy Comprises of Two Steps

Synthesis of compound 5-(4-(phenyl(4-(1,2,2-triphenylvinyl)phenyl)amino)phenyl)furan-2-carbaldehyde (2): A mixture of 4-bromo-N-phenyl-N-(4-(1,2,2-triphenylvinyl)phenyl)aniline (0.5 mol), (5-formylfuran-2-yl)boronic acid (1.0 mol), Pd(dppf)Cl$_2$ (0.05 mol) and K$_2$CO$_3$ (1.5 mol) were dissolved in mixed solvent (MeOH:Toluene=2:2 mL). The reaction was heated to 75° C. for 16 h under nitrogen. When the reaction was completed, the mixture was cooled to room temperature and filtered, of which the solvent was removed by reduced pressure. The residue was dissolved in DCM (50 mL) and washed by water (25 mL×3). The combined organic phase was dried over Na$_2$SO$_4$ and filtered; the filtrate was removed under reduced pressure in order to obtain the crude product, which was further purified by silica gel chromatography (Hex:DCM=5:1) to give product with the yield of 76%. $^1$H NMR (400 MHz, Chloroform-d) δ 9.59 (s, 1H), 7.64 (d, J=8.3 Hz, 2H), 7.29 (d, J=8.9 Hz, 2H), 7.19-6.97 (m, 21H), 6.93 (d, J=8.2 Hz, 2H), 6.84 (d, J=8.3 Hz, 2H), 6.70 (s, 1H).

Synthesis of compound TPE-TFPy: A mixture of 5-(4-(phenyl(4-(1,2,2-triphenylvinyl)phenyl)amino)phenyl)furan-2-carbaldehyde (2) (0.2 mol) and 1,4-Dimethylpyridinium iodide (0.2 mol) was refluxed in ethanol (2 mL) overnight under the catalysis of a few drops of piperidine. After cooling down to room temperature, the solvent was removed and the residue was dissolved and stirred in mixed solvent (Acetone:KPF$_6$=5:5 mL) for 30 min. Then the resultant mixture was purified by chromatography using DCM/MeOH as eluents to afford TPE-TFPy (102 mg) as red solid in 62% yield. $^1$H NMR (400 MHz, DMSO-d$_6$) δ 8.77 (d, J=6.4 Hz, 2H), 8.15 (d, J=6.3 Hz, 2H), 7.86 (d, J=15.9 Hz, 1H), 7.75 (d, J=8.4 Hz, 2H), 7.34 (t, J=7.7 Hz, 2H), 7.27-7.07 (m, 11H), 6.98 (ddd, J=30.9, 16.5, 7.4 Hz, 11H), 6.83 (d, J=8.2 Hz, 2H), 4.20 (s, 3H). $^{13}$C NMR (100 MHz, DMSO-d$_6$) δ 156.06, 150.55, 146.26, 144.75, 144.73, 143.26, 142.83, 140.56, 140.15, 138.66, 131.92, 130.73, 130.64, 129.67, 127.87, 127.80, 127.70, 127.00, 126.59, 126.54, 125.57, 124.54, 123.89, 123.70, 122.86, 122.81, 122.17, 119.57, 119.06, 108.31, 46.66. ESI HRMS: calcd. for C$_{50}$H$_{39}$N$_2$O$^+$ [M−PF$_6$]$^+$: 683.3057, found: 683.3070.

Photophysical Properties and Theoretical Calculation

Figure 2:
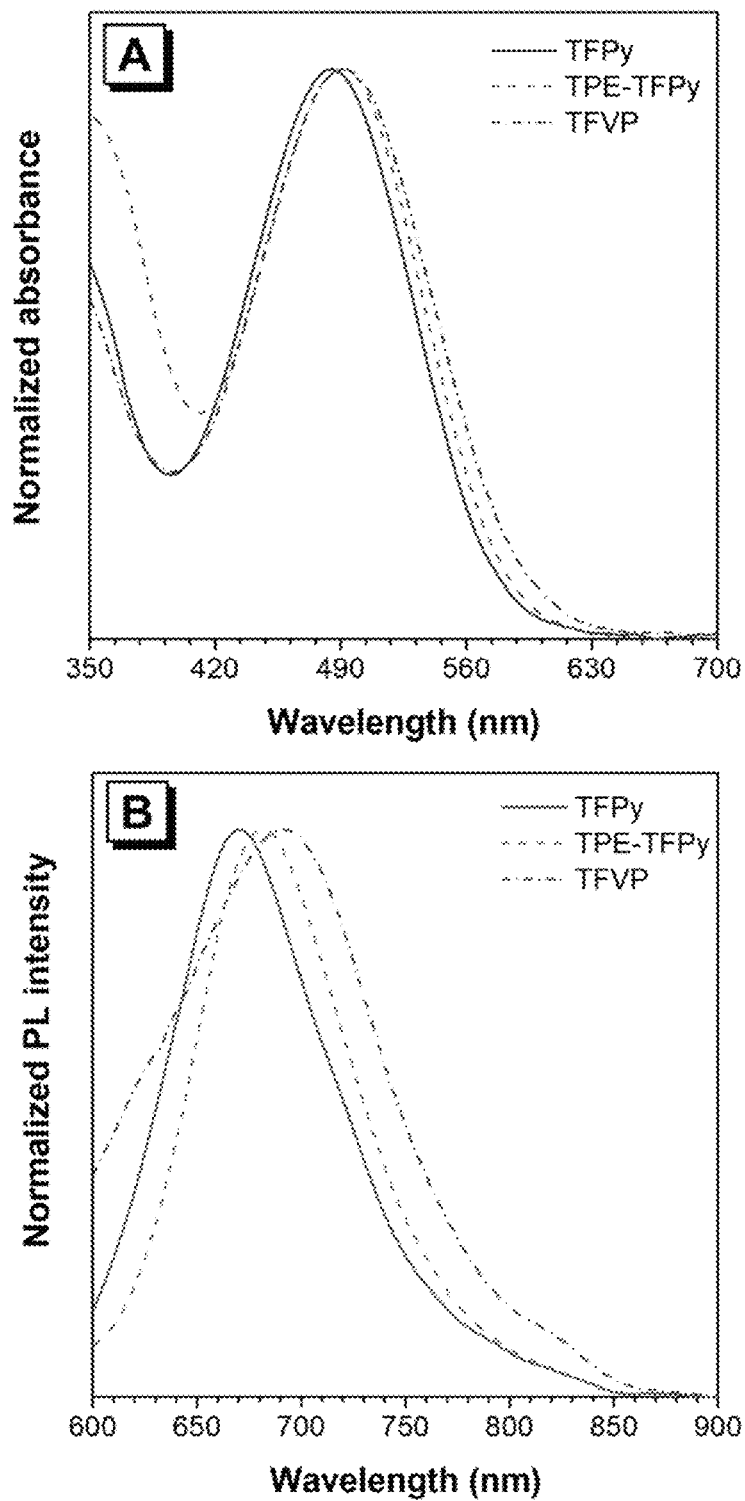
FIG. 2 depicts (A) normalized absorption spectra of TFPy solution in DMSO, TPE-TFPy solution in DMSO and TFVP aqueous solution. (B) Normalized PL spectra of TFPy ($\lambda_{em}$: 672 nm), TPE-TFPy ($\lambda_{em}$: 683 nm), TFVP ($\lambda_{em}$: 690 nm) in solid state. (C) PL spectra of TFVP ($1\times10^{-5}$ M) in $H_2O$/THF mixtures with different THF fractions ($f_T$); $\lambda_{ex}$: 480 nm. (D) Plots of relative PL intensity ($I/I_0$) versus the composition of different solution mixture of TFVP, TPE-TFPy and TFPy. Inset: photos of $H_2O$ and $H_2O$/THF mixture ($f_T$=95%) of TFVP under 365 nm UV light.
Figure 2:
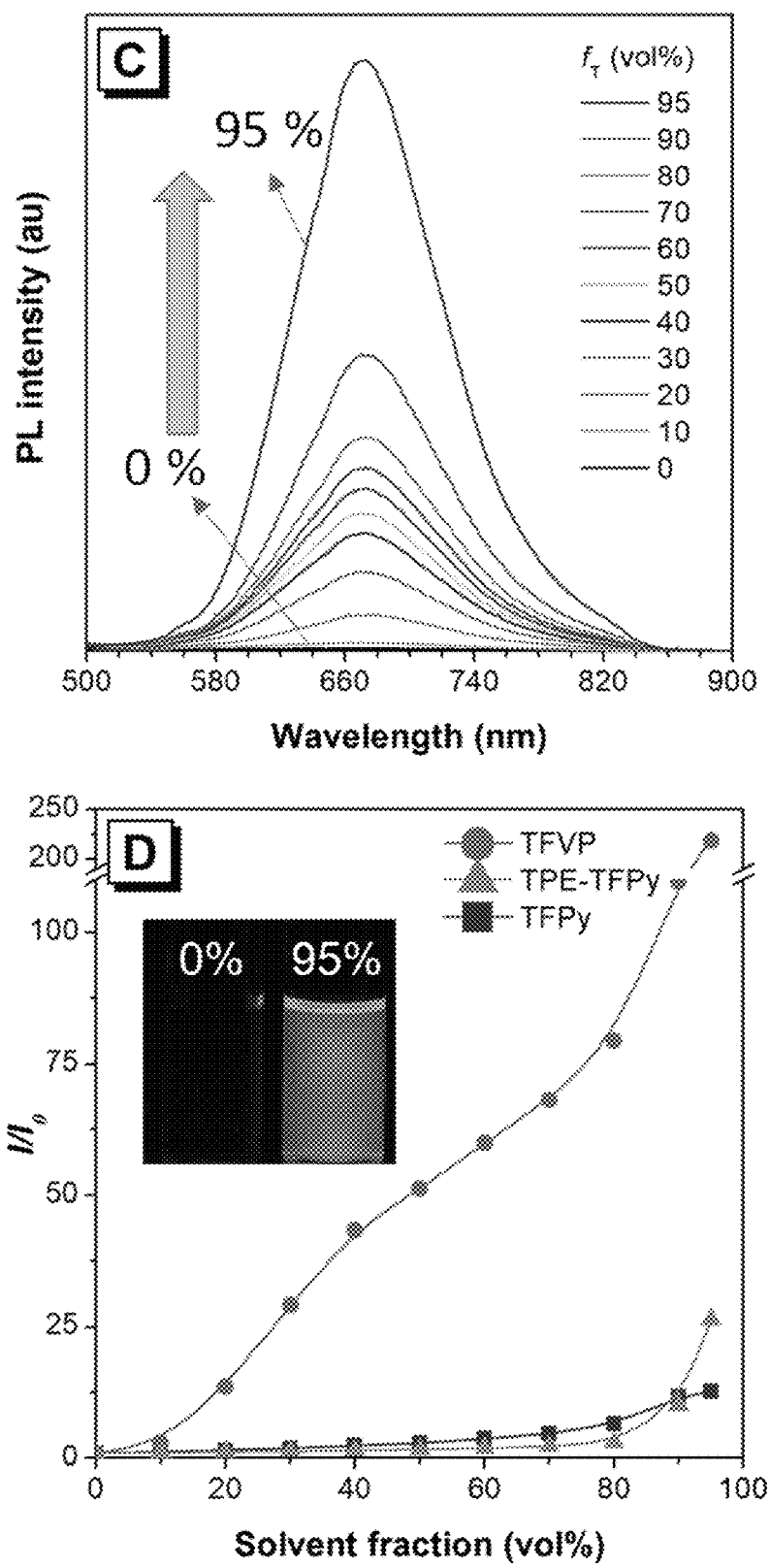
Figure 8:
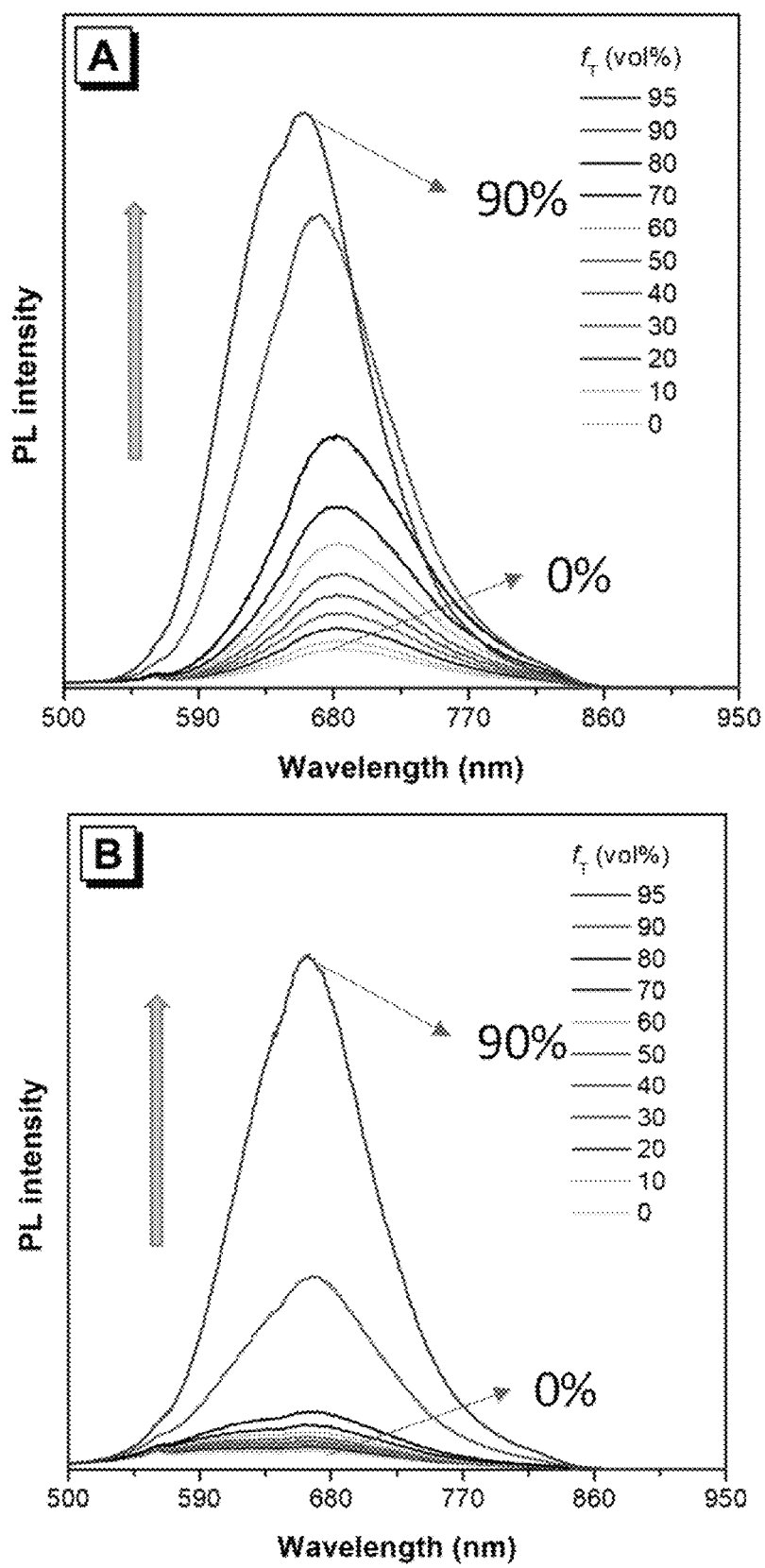
FIG. 8 depicts PL spectra of (A) TFPy and (B) TPE-TFPy ($1\times10^{-5}$ M) in DMSO/toluene mixtures with different toluene fractions ($f_T$); $\lambda_{ex}$: 480 nm.

The photophysical properties of TFPy, TFVP and TPE-TFPy were characterized by UV-Vis and photoluminescence spectroscopies at the concentration of 10 μM as shown in FIG. 2 and summarized in Table 1. The three compounds possess similar absorption with maximum absorption peaks ($\lambda_{abs}$) 1 at 485 nm for TFPy, 492 nm for TFVP, and 490 nm for TPE-TFPy (FIG. 2A). Due to different solubility behavior, the AIE characteristics of TFPy and TPE-TFPy were investigated in DMSO/toluene mixture with different toluene fractions, whereas TFVP was measured in H$_2$O/THF mixture (FIGS. 2C and 2D, FIG. 8). Taking TFVP as an example, TFVP was barely emissive when fully dissolved in water. Upon increasing THF fraction, fluorescence emission intensity got boosted accordingly with a 218-time increment when THF fraction reached 95%. In case of TFPy and TPE-TFPy, the increment value is 12.6 and 26.4, respectively, strongly demonstrating typical AIE characteristics of all three compounds. In addition, upon the increase of THF or toluene as poor solvent, the emission wavelengths of three AIEgens were blue-shifted owing to the decrease of solvent polarity, manifesting TICT attributes, which is again ascribed to their D-A feature. Notably, they exhibit far-red/near-infrared (FR/NIR) emission (672 nm for TFPy, 690 nm for TFVP, and 683 nm for TPE-TFPy) in solid state with relatively large stokes shifts (ca. 200 nm) (FIG. 2B).

TABLE 1

Optical properties of AIEgens TFPy, TFVP and TPE-TFPy.

| AIEgens | Solution | | | | Solid | |
|---|---|---|---|---|---|---|
| | $\lambda_{abs}$ [nm][a] | ε [×10⁴M⁻¹cm⁻¹] | $\lambda_{em}$ [nm][b] $(\Phi_F)^{d)}$ (Soln.) | $\lambda_{em}$ [nm][c] $(\Phi_F)^{d)}$ (Aggr.) | $\lambda_{em}$ [nm] $(\Phi_F)^{d)}$ (Solid.) | $I_{aggr,max}^{e)}/I_{soln}$ |
| TFPy | 485 | 2.7 | 686 (0.4%) | 660 (10%) | 672 (0.5%) | 12.6 |
| TFVP | 492 | 2.8 | 675 (0.4%) | 672 (5%) | 690 (0.6%) | 218 |
| TPE-TFPy | 490 | 3.1 | 672 (0.5%) | 664 (4.2%) | 683 (1.1%) | 26.4 |

[a] Absorption maximum in DMSO (TFPy and TPE-TFPy) and H₂O (TFVP) solution;
[b] Emission maximum in DMSO (TFPy and TPE-TFPy) and H₂O (TFVP) solution at a concentration of 10 μM;
[c] Emission maximum of aggregation state in 5% DMSO + 95% Toluene (TFPy and TPE-TFPy) or 5% H2O + 95% THF (TFVP);
[d] Fluorescence quantum yield determined by a calibrated integrating sphere system;
[e] Emission intensity of aggregation state in 5% DMSO + 95% Toluene (TFPy and TPE-TFPy) or 5% H2O + 95% THF (TFVP).

Figure 7:
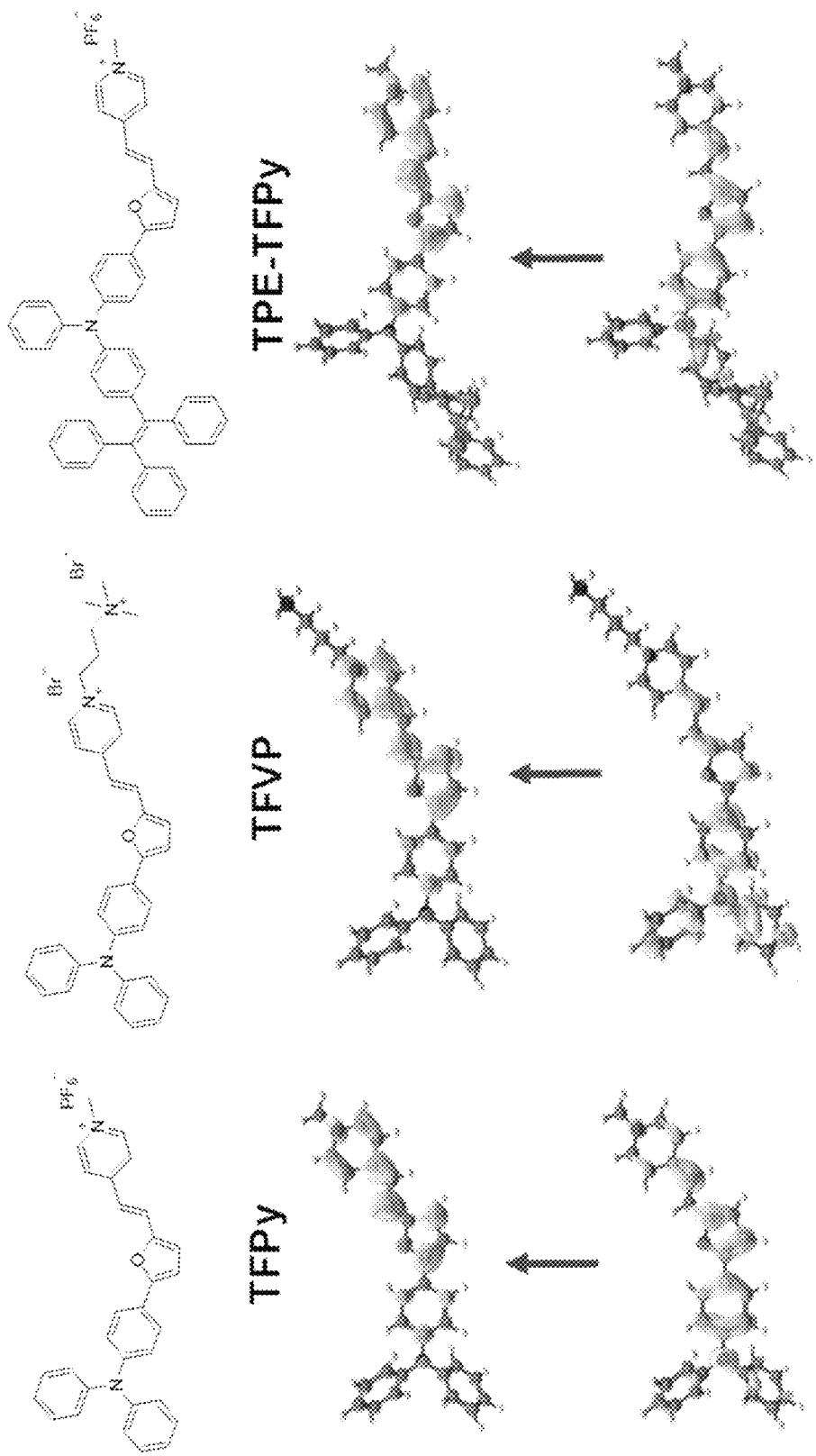
FIG. 7 depicts calculated NTOs of TFPy, TFVP and TPE-TFPy based on Si geometry optimized at the level of ωB97X-D/6-311G*.

To better understand the optical properties of the AIEgens, density functional theory (DFT) calculations were carried out at the level of ωB97X-D/6-311G* with an optimized Si state at TD-ωB97X-D/6-311G* level (FIG. 7). The calculated hole natural transition orbitals (NTOs) of all three molecules delocalize over TPA moiety as well as furan bridge, while electron NTOs are localized at furan region along with pyridine fragment, exhibiting strong charge transfer character. As the quaternary 3-(trimethylammonio) propyl group of TFVP and triphenylethylene group of TPE-TFPy does not contribute much to NTOs, it is speculated that little effect on the emission property would be produced, which is in well accordance with experimental results. For all three AIEgens, the calculated decay energies of ca. 2 eV are relatively small, agreeing with their far red/NIR emission property. Singlet-triplet energy gaps ($\Delta E_{ST}$) are determined to be around 1 eV due to sufficient separation of electron and hole NTOs, potentially making them promising PDT candidates by promoting ROS generation.

Evaluation of Specific Organelle Targeting Ability

Figure 3:
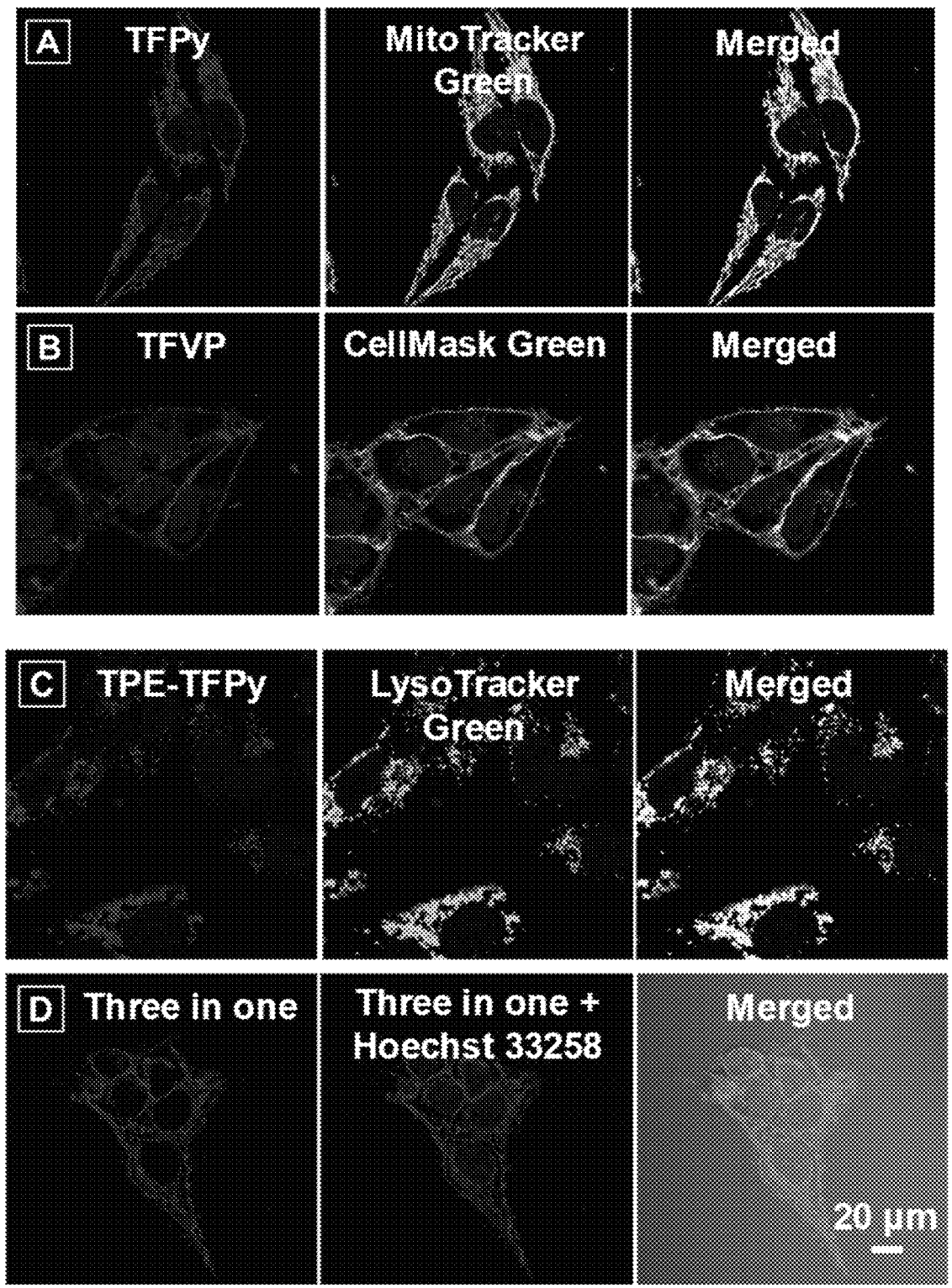
FIG. 3 depicts co-localization test and photostability of TFPy, TFVP and TPE-TFPy. Confocal microscopic images of HeLa cells stained with (A) TFPy (200 nM), MitoTracker Green (50 nM), and their merged images; (B) TFVP (500 nM), CellMask Green (500 nM), and their merged images; (C) TPE-TFPy (2 μM), LysoTracker Green (50 nM), and their merged images; (D) three AIEgens (TFPy, TFVP and TPE-TFPy) altogether, three AIEgens and Hoechst 33258 (5 μM), and their merged images. (E) Loss in fluorescence of HeLa cells stained with TFPy, TFVP, TPE-TFPy, MitoTracker Green, CellMask Green and LysoTracker Green with the number of scans of laser irradiation. Scanning rate: 22.4 s per frame. Scale bar=20 μm.
Figure 3:
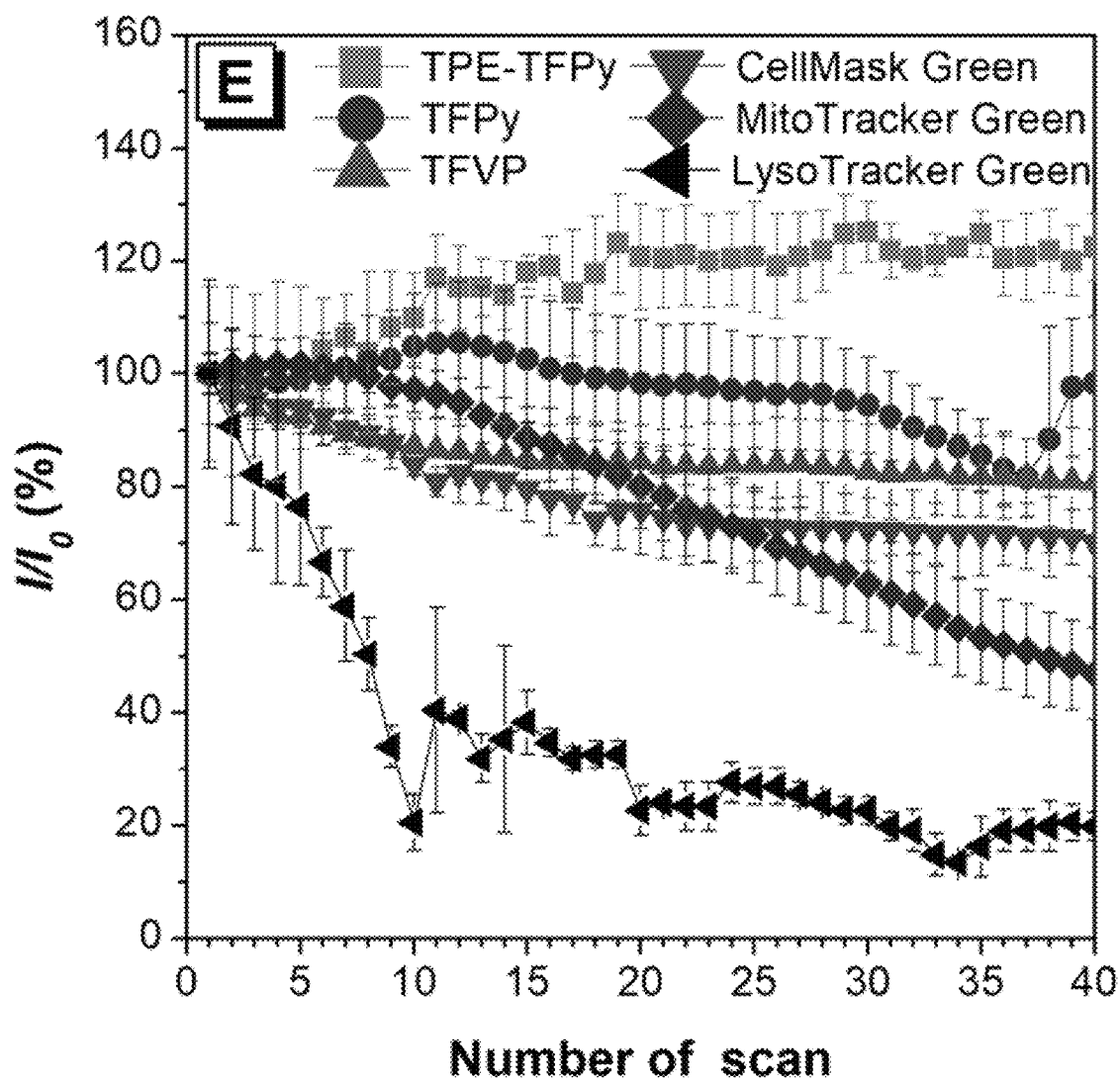

In vitro cellular imaging was carried out to evaluate their subcellular organelle targeting property by confocal laser scanning microscopy (CLSM) using HeLa cell as model cell line. Thanks to the analogous maximum absorption of three AIEgens, fluorescence images can be acquired simultaneously using the same excitation at 488 nm. As illustrated in FIGS. 3A, 3B and 3C, after respective incubations with TFPy, TFVP, and TPE-TFPy, reticulum-like mitochondria, ring-shaped cell membrane, and round or oval-shaped lysosome were clearly visualized showing bright fluorescence and high contrast to background signal. To further prove the targeting specificity, three commercial fluorescent probes, MitoTracker Green, CellMask Green, and LysoTracker Green, were employed to costain with AIEgens respectively. All of three costaining experiments showed perfect overlap as seen in the merged images with the Pearson's correlation coefficients of over 90%, indicating the high targeting specificity of these AIEgens towards given subcellular organelles, also solidly demonstrating that subtle structural alteration can lead to targetability variation. Besides, when HeLa cells were cultured with these three AIEgens simultaneously, all of mitochondria, cell membrane and lysosome were highly emissive (FIG. 3D). It was inferred that the mitochondria-staining behavior of TFPy could be attributed to its high efficiency of electrophoretic transmembrane migration, as well as appropriate binding ability between positively charged pyridinium moiety and the negatively charged interior of the transmembrane potential of mitochondria. The low permeability coefficients resulted from the quite high free energy barrier of TFVP at membrane center could lead to its specific accumulation. In the case of TPE-TFPy, it tends to form nano-sized aggregates in culture media due to the high hydrophobicity, and the in-situ generated aggregates can internalize into lysosome of HeLa cells through endocytosis and specifically light up lysosome upon photoexcitation.

Figure 4:
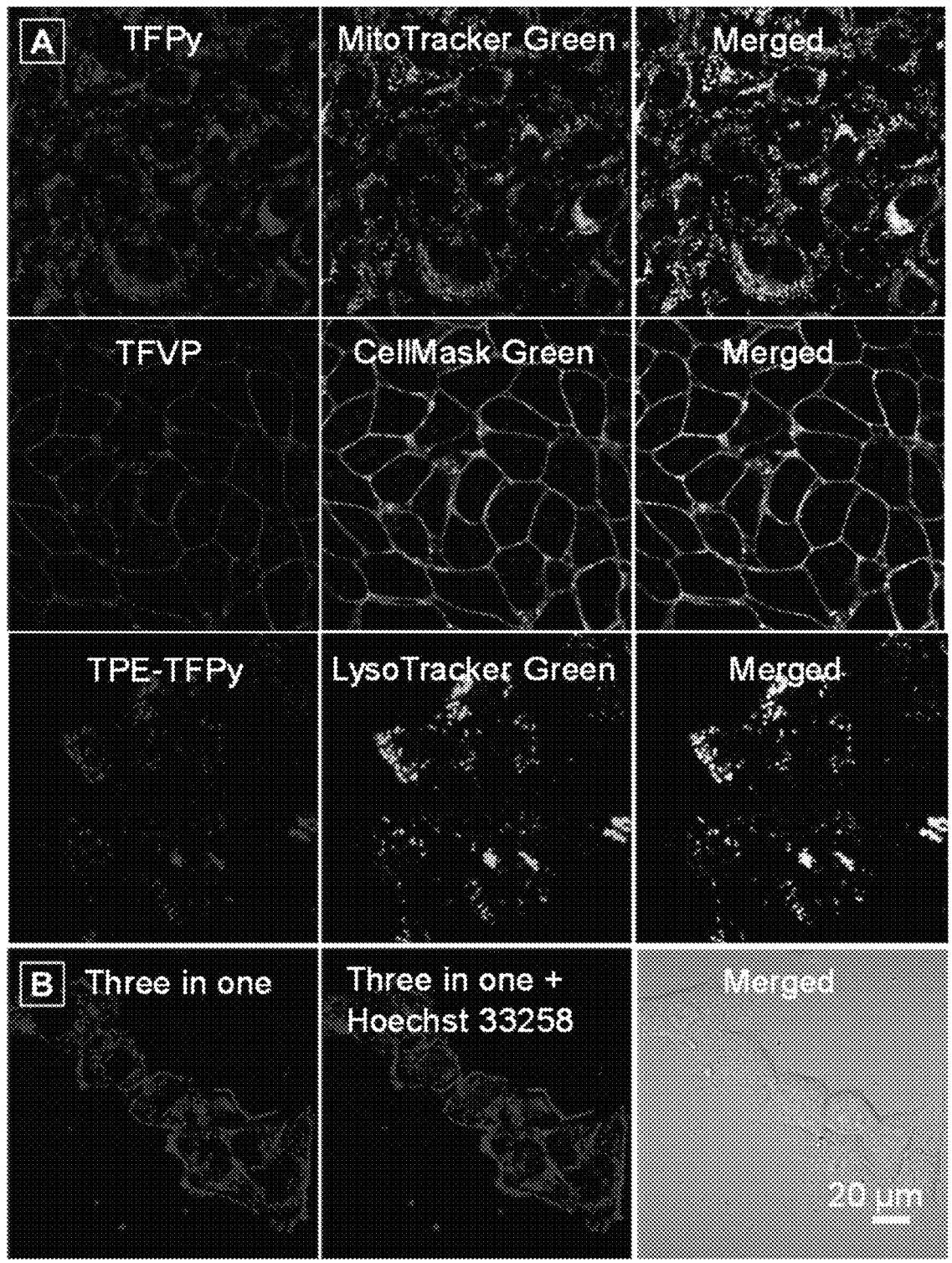
FIG. 4 depicts co-localization test of TFPy, TFVP and TPE-TFPy. Confocal microscopic images of 4T1 cells stained with (A) TFPy (1 μM), MitoTracker Green (500 nM), and their merged images; TFVP (5 μM), CellMask Green (500 nM), and their merged images; TPE-TFPy (2 μM), LysoTracker Green (500 nM), and their merged images; (B) three AIEgens (TFPy, TFVP and TPE-TFPy) altogether, three AIEgens and Hoechst 33258, and their merged images. Scale bar=20 um.

Motivated by the excellent targetability and specificity of three diverse organelle-targeting AIEgens, photostability was also carefully investigated as it is an essential parameter to evaluate a fluorescence imaging agent. Photostability assessment was carried out by continuous irradiation and sequential scanning with confocal microscope. After 40 times of scan, it was observed that minimal intensity loss was found for TPE-TFPy, TFPy and TFVP, whereas three fluorescent commercial probes especially LysoTracker Green suffered obvious fluorescence intensity decrease, demonstrating high photobleaching resistance of AIEgens (FIG. 3E). With HeLa cell imaging and photostability data in hand, additional cellular uptake experiment using 4T1 cell line was performed as preliminary study for in vivo experiment. Similar bioimaging results were obtained, that is, TFPy, TFVP and TPE-TFPy exhibited strong affinity towards mitochondria, cellular membrane, and lysosome, respectively to produce bright red fluorescence. The AIEgens exhibit high targeting specificity which was confirmed by superb costaining outcome with commercial probes (FIG. 4A). Again, with three AIEgens staining jointly, the mitochondria, cellular membrane, and lysosome were well located and lighted up concurrently.

In Vitro and In Vivo Photodynamic Therapy

In general, each organelle has its own specific function to manage cellular behavior. Briefly speaking, mitochondria is a "power house" that can produce ATP to regulate cellular metabolism. Plasma membrane has selective permeability that protect the interior of cell from environment. Lysosome's acidic interior can degrade obsolete biomolecules by various enzymes. All of the above mentioned three organelles are of vital importance to cellular status, therefore applying PDT to these regions can effectively induce cancer cell ablation. We are thereby prompted to examine PDT efficacy of three AIEgens, and more importantly, to explore whether PDT effectiveness will be boosted if three AIEgens are introduced concurrently.

Figure 5:
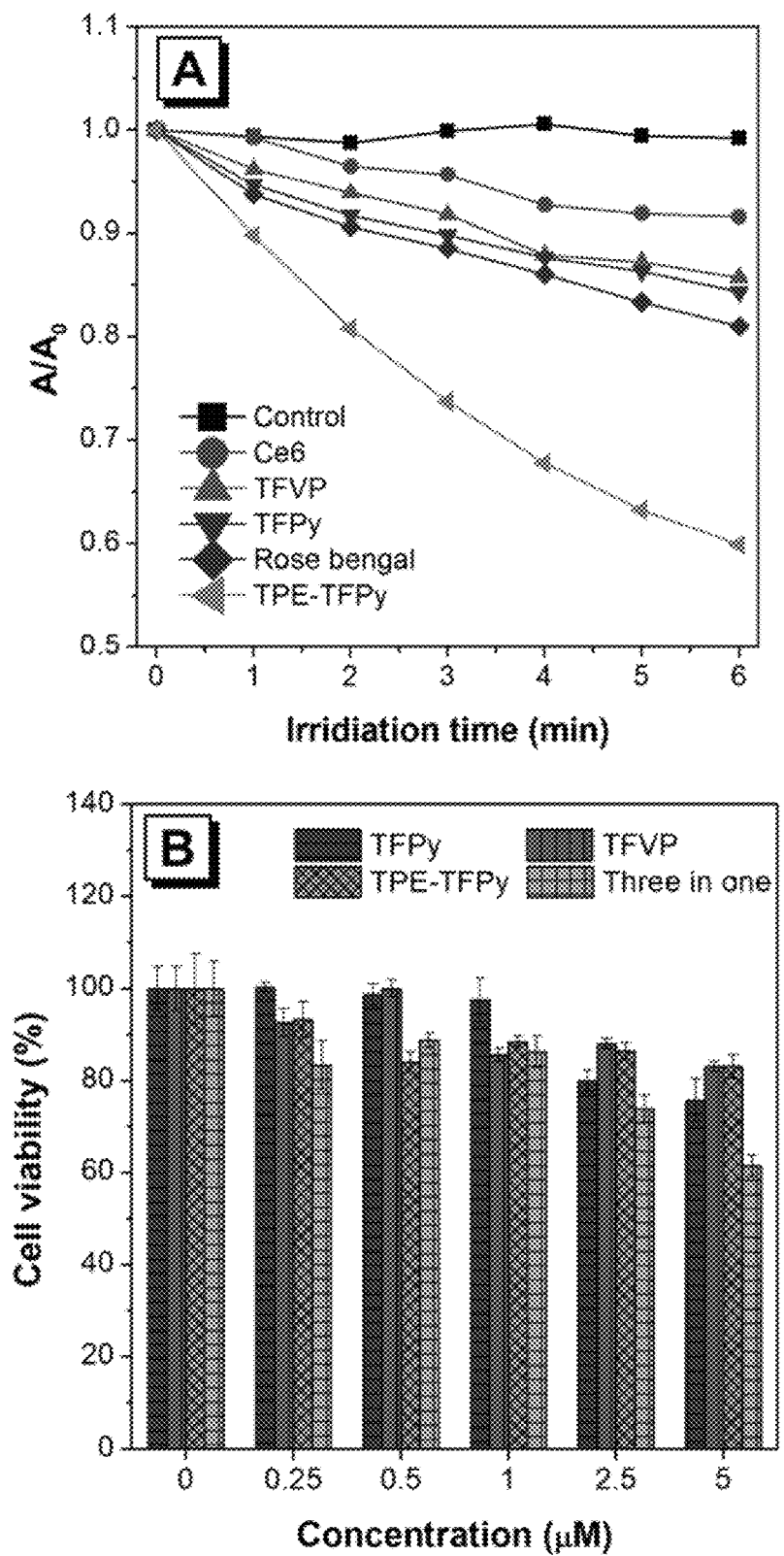
FIG. 5 depicts (A) normalized absorbance intensity of ABDA at 380 nm after photodecomposition by ROS upon white light irradiation. Cell viability of HeLa cell stained with different concentrations of AIEgens in the (B) absence and (C) presence of white light irradiation. Cell viability of 4T1 cell stained with different concentrations of AIEgens in the (D) absence and (E) presence of white light irradiation.
Figure 5:
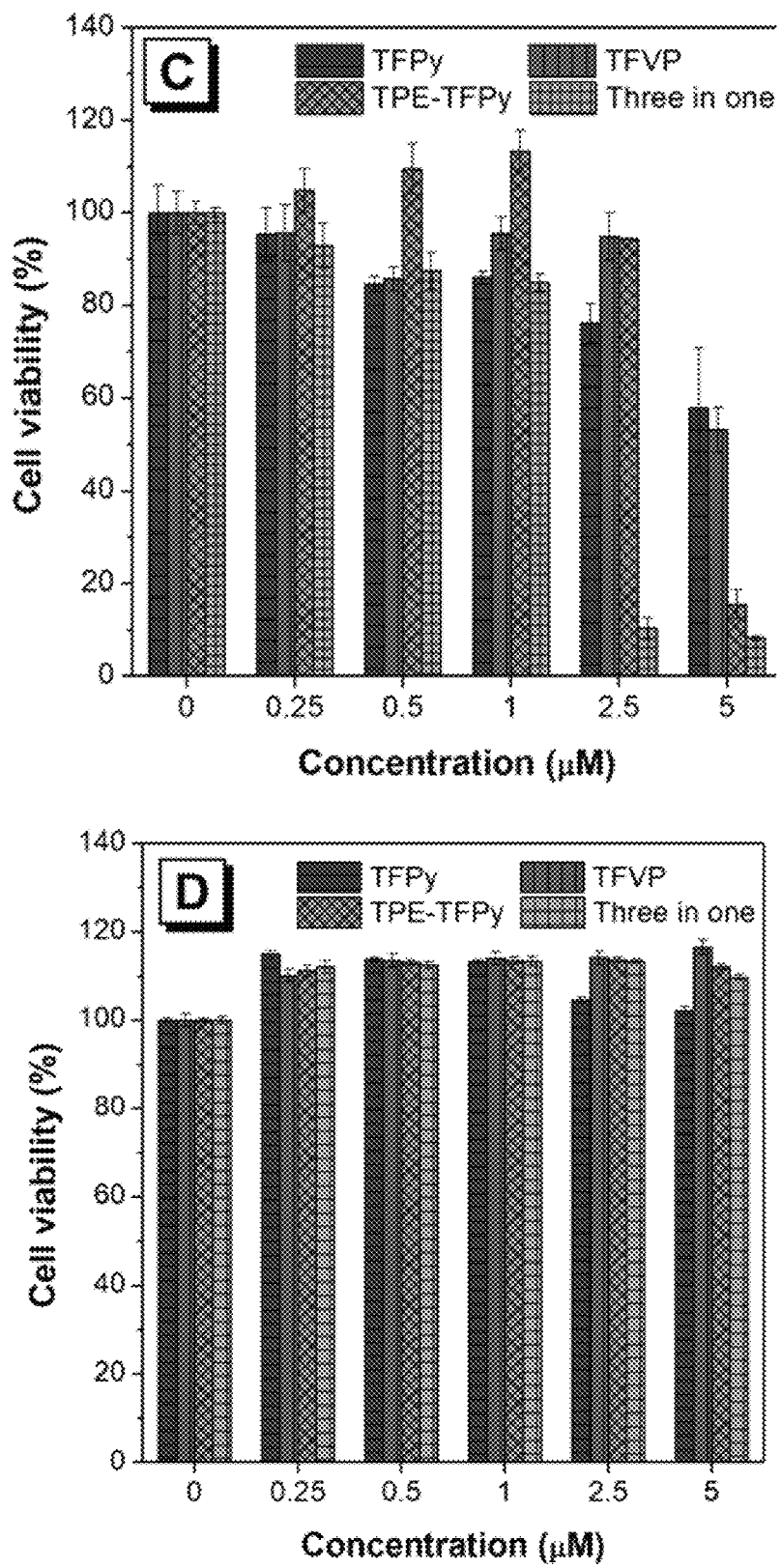
Figure 5:
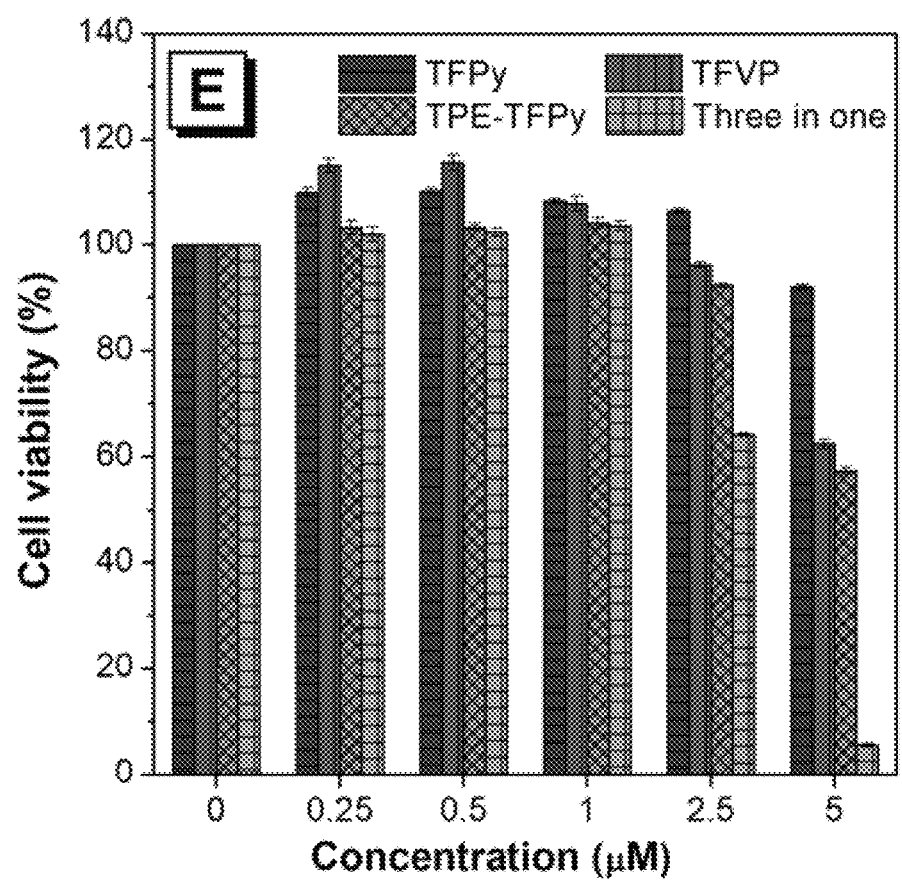
Figure 9:
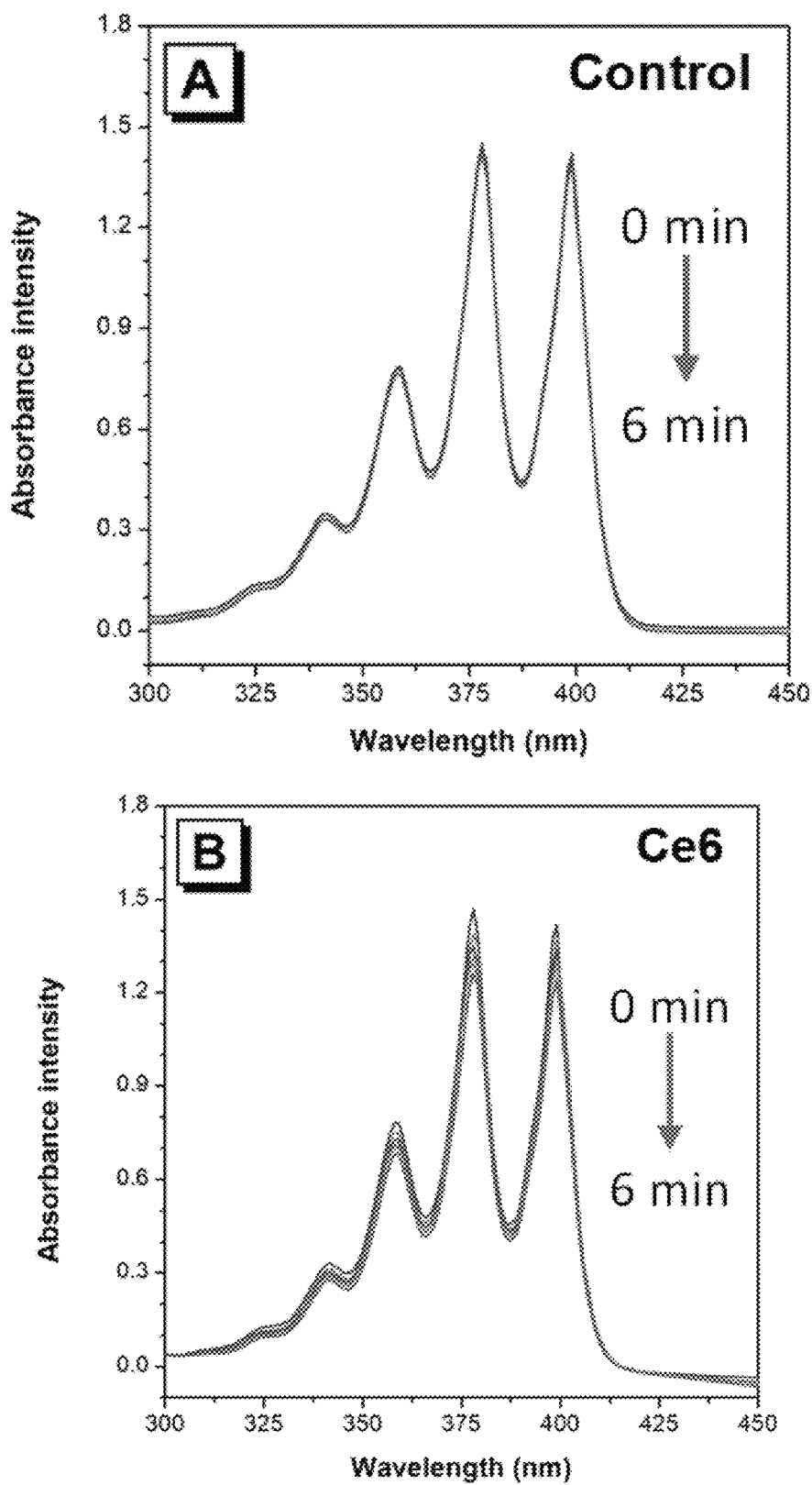
FIG. 9 depicts (A) UV-vis spectra of ABDA in the absence of PSs under white light irradiation in DMSO/water (v:v)= 1/100. UV-vis spectra of ABDA in the presence of (B) Ce6 or (C) Rose Bengal or (D) TFPy or (E) TFVP or (F) TPE-TFPy under white light irradiation in DMSO/water (v:v)=1/100. [AIEgens or Ce6 or Rose Bengal]=$1\times10^{-6}$ M, [ABDA]=$1\times10^{-5}$ M, time interval for recording the UV-vis spectra: 60 s.
Figure 9:
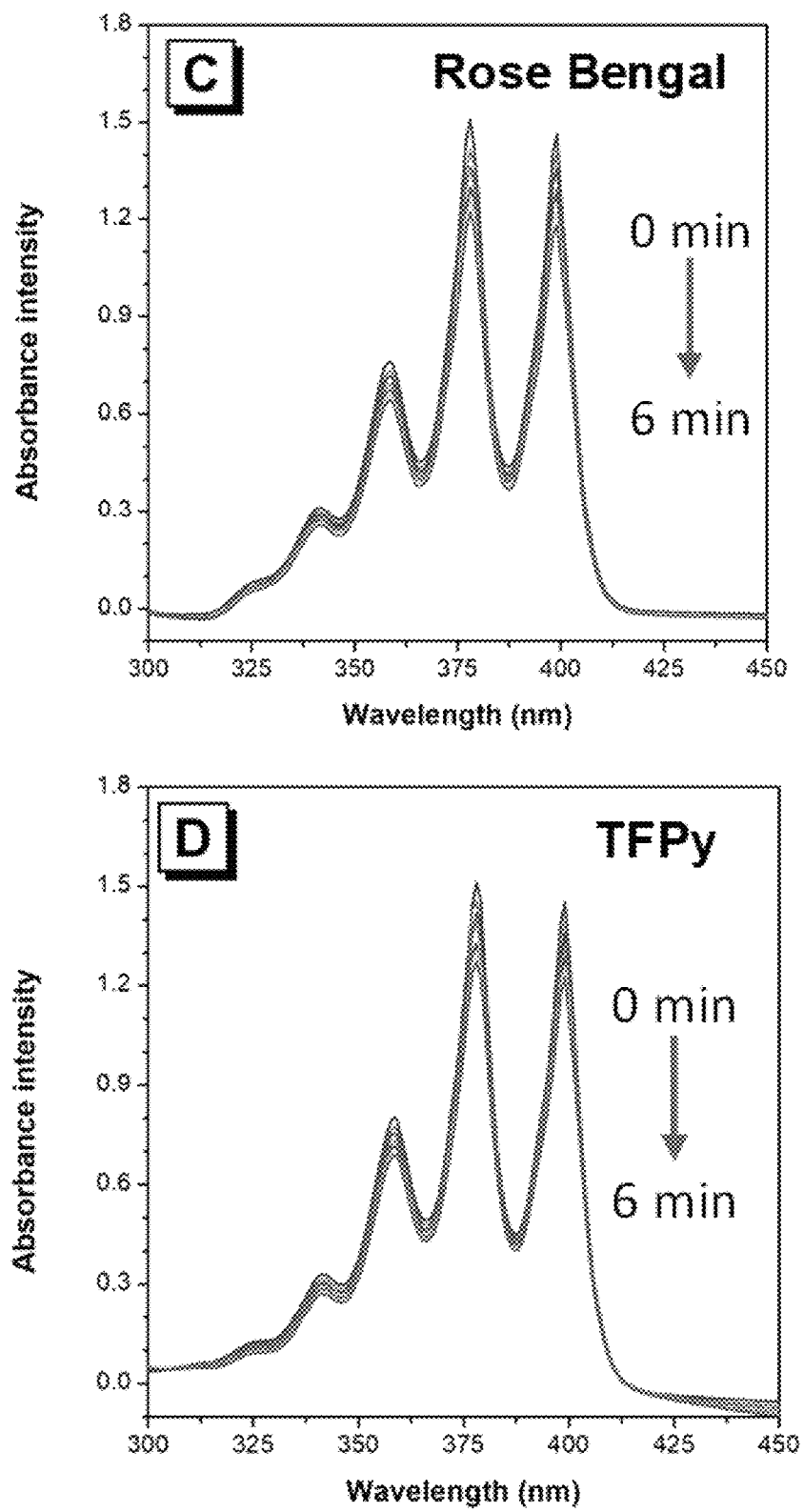
Figure 9:
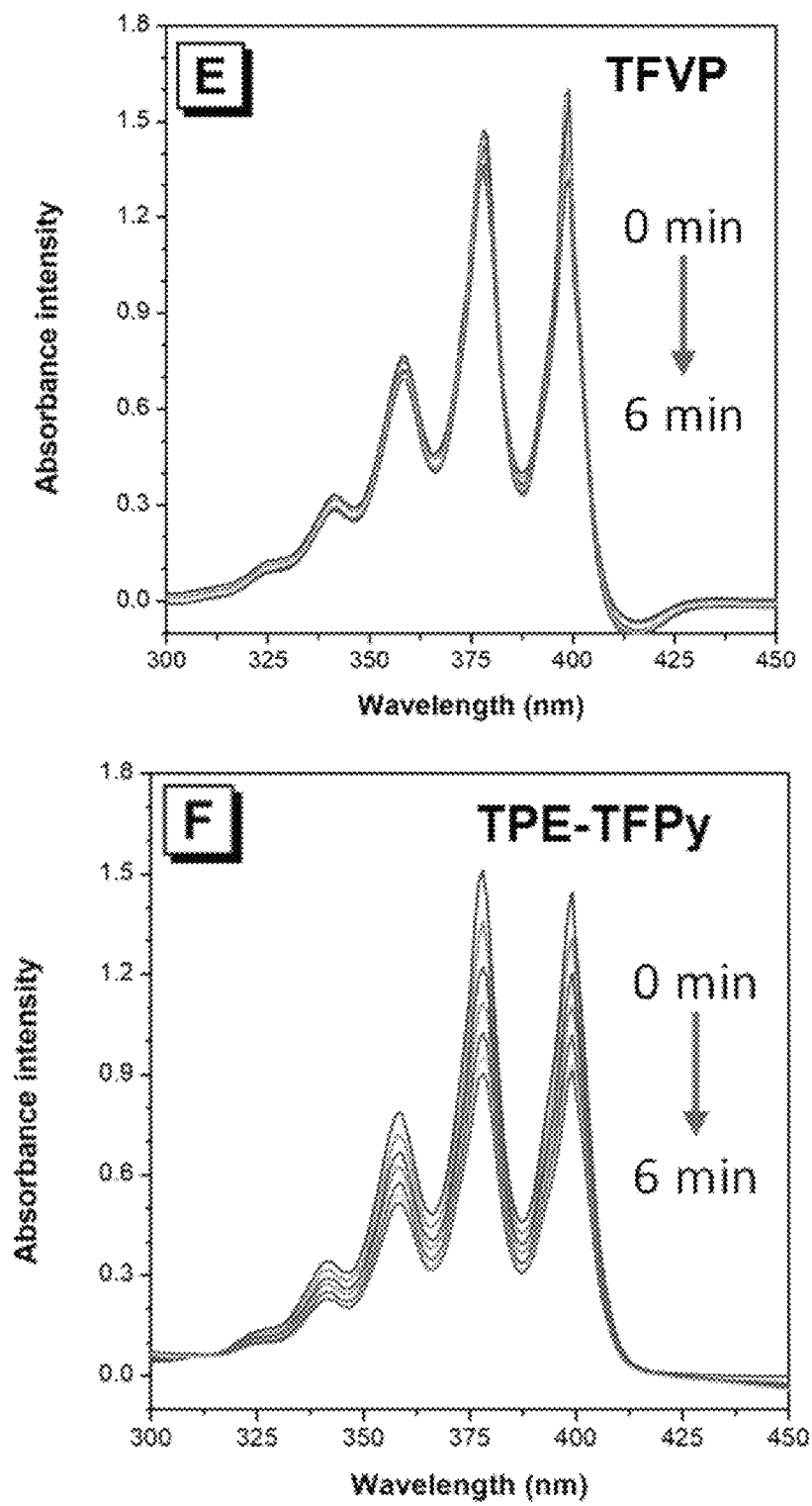

Preliminary study was conducted by evaluating capability of ROS generation of three AIEgens. 9,10-Anthracenediyl-bis-(methylene)-dimalonic acid (ABDA) whose absorption will decrease once oxidized by ROS was utilized as an indicator. Upon white light irradiation (4.2 mW·cm$^{-2}$), absorption peak of ABDA at 378 nm gradually decreased along with irradiation time in the presence of photosensitizers, while no obvious absorbance intensity change was found for control group (FIG. 5A and FIG. 9). Ce6 and Rose Bangel, two well-known commercially available standard photosensitizers, were engaged as comparison. Both TFPy and TFVP exhibiting similar ROS generation efficacy were better than Ce6, but not as efficient as Rose B angel. In addition, a sharp decline of absorbance intensity was found in the case of TPE-TFPy, and its ROS generation capability was much higher than Rose Bangel, suggesting the superior ROS generation performance and great potential for PDT application.

Cytotoxicity of photosensitizer is a non-negligible factor to take into consideration. Desired photosensitizer should exhibit minimal cytotoxicity under dark condition, but produce efficient ROS to induce cell death upon light irradiation. Consequently, quantitative evaluation of PDT effect was applied on both HeLa Cell and 4T1 cell line through standard methylthiazolyldiphenyltetrazolium bromide (MTT) assay. Each AIEgen and an experimental group named "three in one" were evaluated. The "three in one" group was comprised of one third concentration of each AIEgen (⅓ TFPy, ⅓ TFVP, and ⅓ TPE-TFPy) to assure the overall concentration as same as other experimental groups. As illustrated in FIGS. 5B and 5D, after incubation for 24 h, negligible cellular viability reduction was found for HeLa cell with the concentration as high as 2.5 µM. In the case of 4T1 cell, the viability maintained 100% at a concentration of 5 µM, suggesting little toxicity of these AIEgens towards both cell lines under dark condition. However, upon irradiation with light for 20 min, HeLa cell suffered severe viability loss with only 10% remained when the "three in one" group was at a concentration of 2.5 µM (FIG. 5C). Meanwhile, each individual AIEgen only exhibited moderate PDT efficacy. TPE-TFPy was outstanding among the three AIEgens, as it caused cell viability to drop rapidly to 15% at a concentration of 5 µM while that of TFPy and TFVP were 58% and 53%, respectively, which is consistent with its superior ROS generation ability. As for 4T1 cell, cell viability of "three in one" group started to decline at a concentration of 2.5 µM, and almost complete cell death was induced at concentration of 5 µM (FIG. 5E). Nevertheless, the individual AIEgen hardly displayed any therapeutic effect at 2.5 µM, and more than 60% cell viability still remained at 5 µM. Interestingly, ROS generation degree of "three in one" group was not as much as TPE-TFPy, but it caused more cell death. The above results not only quantitatively demonstrated ROS generation ability and in vitro PDT effect of three AIEgens, but provided strong evidence that three-pronged PDT deriving out of multiple organelles can induce enhanced therapeutic effect as well.

Figure 6:
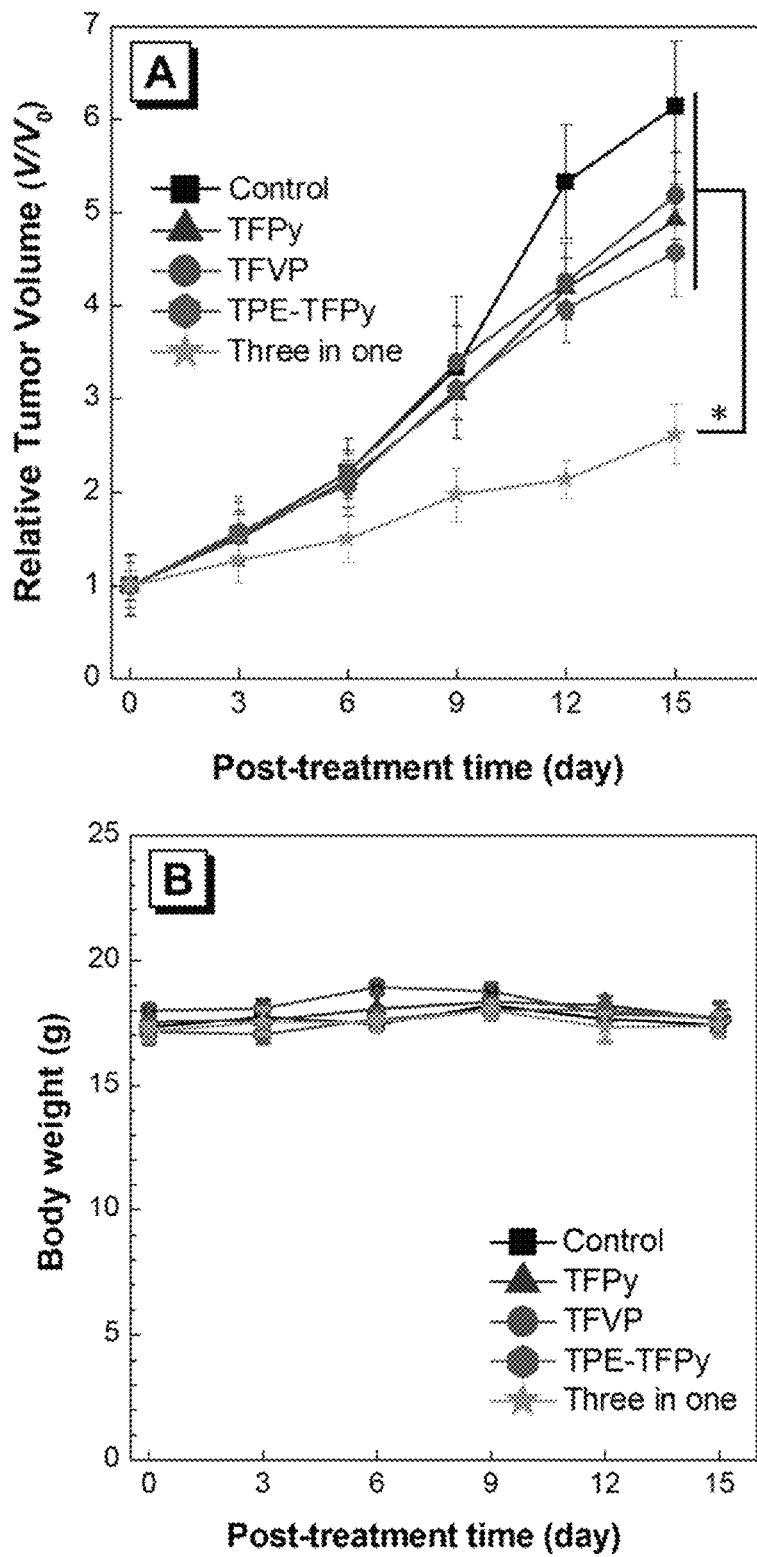
FIG. 6 depicts (A) Tumor growth curves and (B) body weight changes of mice in different treatment groups. * represents P<0.05, in comparison between three in one group and other treatment groups.
Figure 10:
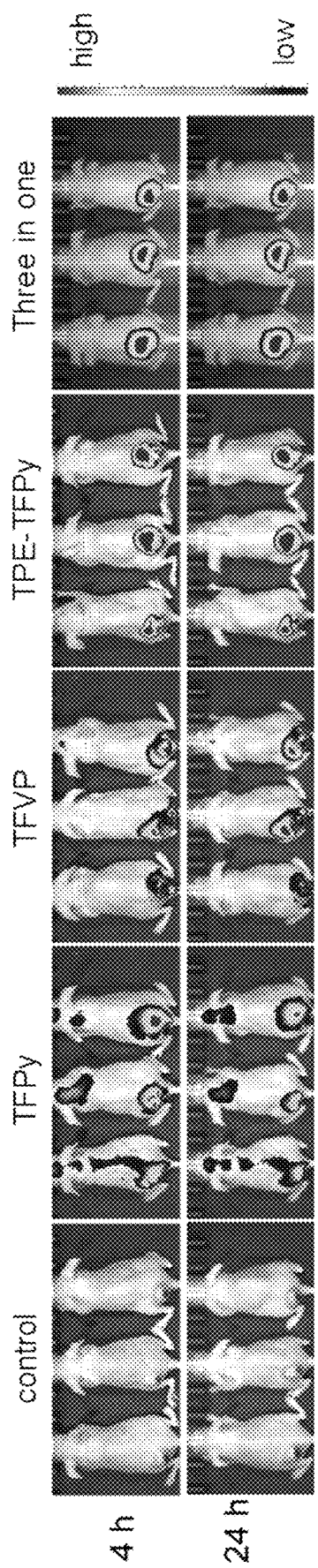
FIG. 10 depicts respective fluorescence images of tumor-bearing mice after intratumor injection of TFPy, TFVP, TPE-TFPy, and three in one at different time points as indicated.
Figure 11:
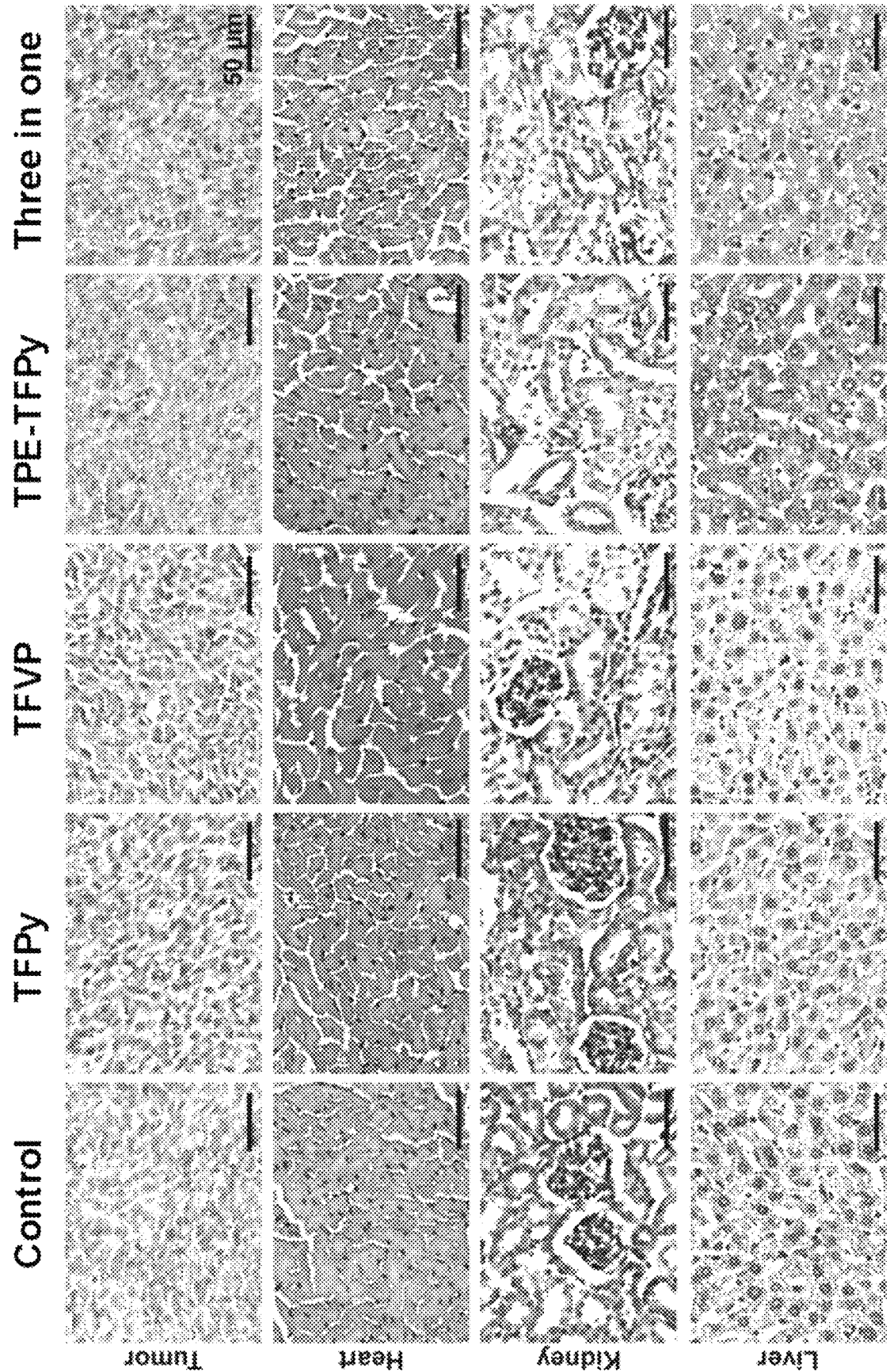
FIG. 11 depicts histological H&E staining of tumor as well as major organs slices on day 15 post treatment.
Figure 11:
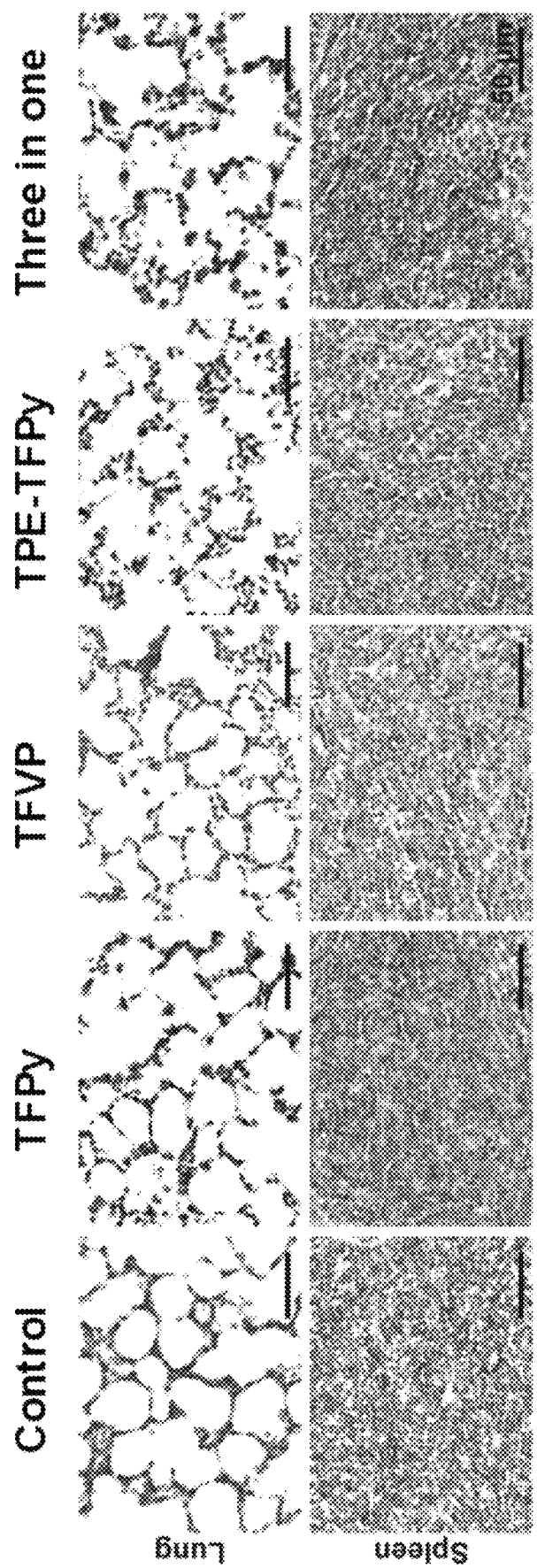

Aiming to figure out whether combination enhanced PDT can be applied above cellular level, in vivo therapy experiment was conducted based on 4T1 breast tumor model, which is a suitable and popular experimental tumor model as its progressive spread feature is very similar to that of human mammary cancer. Tumor-bearing mice were divided into five groups, with one control group injecting water alone and four experimental groups (namely TFPy, TFVP, TPE-TFPy, and "three in one") injecting photosensitizers' aqueous solution (10$^{-4}$ M, 100 µL). As depicted in FIG. 10, after intratumor injection, intense fluorescence signals were captured at the tumor site in each case. At 24 h post-injection, tumor fluorescence was still significant, indicating the remarkable tumor retention properties of these AIEgens. In the following study, tumor sites were exposed to white light irradiation for 10 min. As the treatment proceeded, tumor sizes were measured and evaluated every three days. It was found that all of the four experimental groups were able to control cancer cell proliferation in comparison with control group. It is worthy to note that the "three in one" group herein again manifested strong hindrance of tumor growth to a greater extent than each photosensitizer alone, making combination enhanced PDT a convincing strategy to improve anti-tumor efficacy (FIG. 6A). Moreover, body weight was monitored for each group to assess the toxicity, since low toxicity is of vital importance to practical use. As shown in FIG. 6B, no obvious body weight loss or difference was observed among different groups, owing to minimal toxicity of PDT approach. After 15 days of treatment, mice were sacrificed and major organs were sliced for histological hematoxylin and eosin (H&E) staining. All the tissue sections including heart, kidney, liver, lung, and spleen were evaluated, where no pathological change was observed (FIG. 11). The body weight and H&E result above thus indicate that the photosensitizers, either individual or combined, were highly biocompatible.

What is claimed is:

1. An aggregation-induced emission luminogen (AIEgen) selected from the group consisting of:

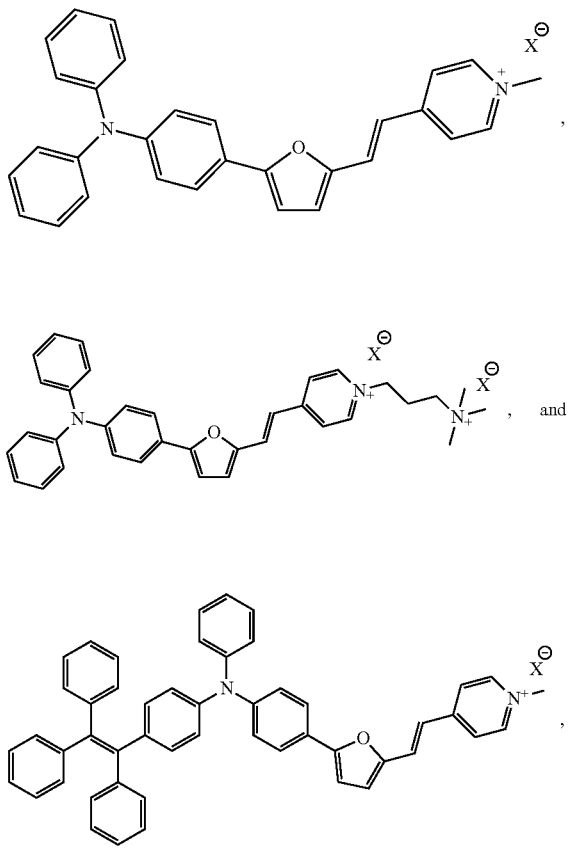

wherein X for each occurrence is independently an anion.

2. A composition comprising two or more AIEgen of claim 1.

3. The composition of claim 2, wherein the two or more AIEgen are:

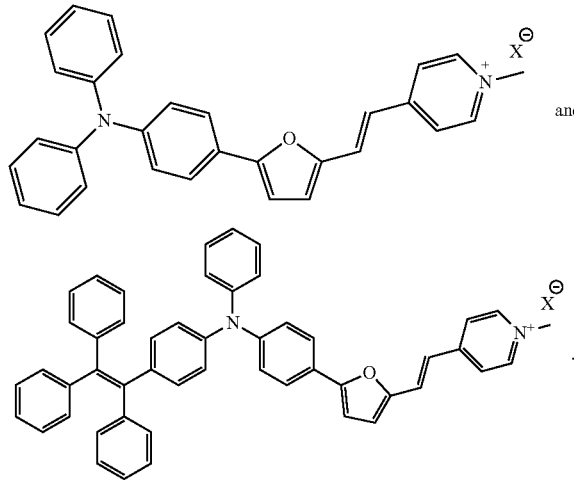

and

4. The composition of claim 3 further comprising:

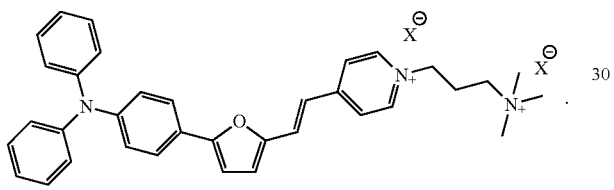

5. A pharmaceutical composition comprising at least one AIEgen of claim 1 and at least one pharmaceutically acceptable excipient.

6. A pharmaceutical composition comprising the composition of claim 2 and at least one pharmaceutically acceptable excipient.

7. A method of treating a cancer cell, the method comprising: contacting the cancer cell with a therapeutically effective amount of at least one AIEgen of claim 1; and irradiating the cancer cell with electromagnetic radiation in the presence of oxygen.

8. A method of imaging a cell, the method comprising: contacting the cell with at least one AIEgen of claim 1; irradiating the cell with electromagnetic radiation; and detecting luminescence from the at least one AIEgen.

9. A method of preparing an AIEgen of claim 1, the method comprising: contacting a compound having Formula 4:

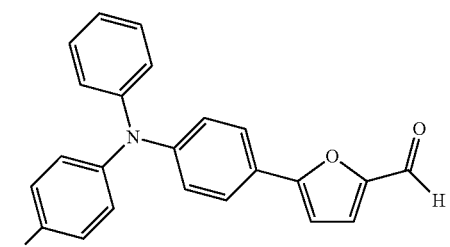

wherein
$R^2$ is selected from the group consisting of hydrogen and $R^8$; and
$R^8$ represents a moiety having the structure:

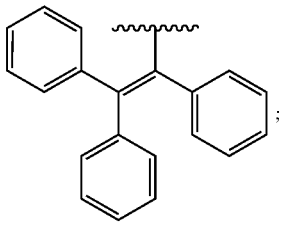 [SMILES: *C(=C(c1ccccc1)c1ccccc1)c1ccccc1]

with a secondary amine and a compound of Formula 5a or 5b:

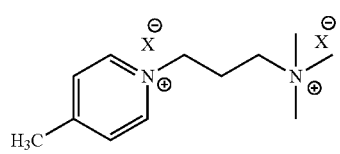

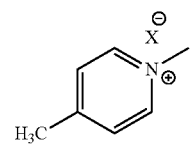

wherein X for each occurrence is independently an anion.

* * * * *